(12) United States Patent
Miyazaki et al.

(10) Patent No.: US 6,445,761 B1
(45) Date of Patent: Sep. 3, 2002

(54) X-RAY COMPUTERIZED TOMOGRAPH INCLUDING COLLIMATOR THAT RESTRICTS IRRADIATION RANGE OF X-RAY FAN BEAM

(75) Inventors: Osamu Miyazaki, Kitasoma-gun; Tetsuo Nakazawa, Kashiwa; Yoshihiro Goto, Tokyo, all of (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/380,824

(22) PCT Filed: Mar. 11, 1998

(86) PCT No.: PCT/JP98/01004

§ 371 (c)(1),
(2), (4) Date: Sep. 10, 1999

(87) PCT Pub. No.: WO98/40013

PCT Pub. Date: Sep. 17, 1998

(30) Foreign Application Priority Data

Mar. 12, 1997 (JP) .............................................. 9-057540
Jul. 9, 1997 (JP) .............................................. 9-183845

(51) Int. Cl.[7] .................................................. A61B 6/00
(52) U.S. Cl. ............................................ 378/8; 378/16
(58) Field of Search ................................... 378/8, 4, 901, 378/15, 16, 20, 147, 150, 152

(56) References Cited

U.S. PATENT DOCUMENTS

| 4,394,738 A | | 7/1983 | Wagner |
| 5,485,493 A | | 1/1996 | Heuscher et al. |
| 5,528,644 A | * | 6/1996 | Ogawa et al. ................. 378/8 |

FOREIGN PATENT DOCUMENTS

| FR | 2 700 259 | | 7/1994 |
| JP | 58-46947 A | * | 3/1983 |
| JP | 58-183145 A | * | 10/1983 |
| JP | 3-39011 A | * | 4/1991 |

* cited by examiner

*Primary Examiner*—David P. Porta
(74) *Attorney, Agent, or Firm*—Antonelli, Terry, Stout & Kraus, LLP

(57) ABSTRACT

An X-ray CT apparatus including a collimator that restricts an irradiation range of an X-ray fan beam, in which first projection data is obtained with no restriction placed onto the X-ray irradiation range through the collimator, then, second projection data is obtained with the X-ray irradiation range restricted in accordance with a concerned region set on a tomographic image, and when reconstructing an image with the use of the second projection data, the image is reconstructed using, as data outside of the concerned region, data of a corresponding portion of the first projection data.

27 Claims, 19 Drawing Sheets

X-RAY COMPUTERIZED TOMOGRAPH INCLUDING COLLIMATOR THAT RESTRICTS IRRADIATION RANGE OF X-RAY FAN BEAM

TECHNICAL FIELD

The present invention relates to an X-ray CT (computerized tomograph) that obtains an in-body tomographic image of a patient with the use of an X-ray. More particularly, it relates to an X-ray CT that, when continuously measuring almost the same cross section, suppresses the X-ray irradiation toward a region outside a set concerned region up to the smallest possible degree, thereby making it possible to reduce an X-ray exposure dose toward the patient, an operator or a specific tissue.

BACKGROUND ART

The X-ray CT has already been used widely in fields such as medical care. For example, in recent years, when endermically executing biopsy of a nidus or the treatment thereof, the X-ray CT is used as the guide to a puncture. Executing, in this way, the biopsy of a nidus or the treatment thereof under the guide by the X-ray CT is now considered to be an effective and helpful method, since this method can be expected not only to shorten an operation time but also to enhance accuracy of the operation.

By the way, for guidance by the X-ray CT, there exist two methods. One method is a method in which the puncture and the CT scanning are repeated alternately and intermittently, while confirming data such as a position of tip of a puncture needle. The other method is a method in which the CT scanning is performed continuously and the image is sequentially displayed so that the position of tip of the puncture needle can be confirmed immediately (CT fluoroscopy). In particular, the latter method permits the tomographic image to be obtained on a real time basis, thus bringing about an advantage of shortening the operation time even further.

However, in the methods where the CT scanning is executed intermittently or continuously as are described above, an increase in the X-ray exposure dose, which is caused by the intermittent or the continuous CT scanning, has become a problem to the patient or the operator. The X-ray exposure dose is determined by the X-ray irradiation dose and slice width set by a slice collimator. In order to reduce the exposure dose, it is sufficient to decrease the irradiation dose just by decreasing a tube electric current passing through an X-ray tube. The decrease in the irradiation dose (mAs=mA×sec), however, means an increase in the noise by X-ray fluctuation. This, accordingly, has resulted in a problem that picture quality of the tomographic image has been deteriorated exceedingly.

DISCLOSURE OF THE INVENTION

Then, in view of the above-mentioned problems in the conventional techniques, it is an object of the present invention to provide an X-ray CT that is capable of reducing the X-ray exposure dose toward the patient or the operator without causing the deterioration of picture quality of the obtained tomographic image even if the X-ray photography is executed continuously or intermittently at the time of operations such as the above-described puncture based on guidance by the X-ray CT.

According to the present invention, in order to accomplish the above-mentioned object, an X-ray CT is provided that rotates an X-ray source continuously to measure projection data of a subject continuously over a plurality of times and, based on the projection data, reconstructs a tomographic image of the subject to sequentially display it on a display, including a concerned region setting unit that sets, within the subject, an irradiation range of an X-ray emitted from the X-ray source, and an X-ray shielding apparatus, i.e. a channel collimator, that, when rotating the X-ray source to measure the projection data, restricts an irradiation range of a fan beam so as to suppress X-ray irradiation outside of the concerned region set by the concerned region setting unit.

Also, in the present invention, there is provided an image processor that, when a measurement is performed with the X-ray fan beam converged on the concerned region, makes it possible to reconstruct a tomographic image in a region with the use of measurement data obtained previously. The region exists outside of the set concerned region, and the channel collimator suppresses the X-ray irradiation toward the region. The image processor also displays the tomographic image in the region.

Further, in the present invention, in the course of said plural times of continuous measurements, the channel collimator is so controlled as to obtain projection data acquired by normal photography (global measurement scanning) or projection data in a region that is wider as compared with the concerned region, the normal photography being not restricted to the X-ray irradiation region set by the concerned region setting unit.

Moreover, in the present invention, the projection data are measured by irradiating the subject with X-rays while gradually reducing or expanding the X-ray irradiation range between the concerned region set by the concerned region setting unit and the global measurement scanning range.

Furthermore, in the present invention, there is provided an image processor that is capable of reconstructing projection data in a region outside of the concerned region through extrapolation from scanned data obtained by irradiating only the concerned region with X-rays.

In addition, in the present invention, the concerned region setting unit is configured to display on the display a boundary between the inside and the outside of the set concerned region.

Namely, in the present invention, the concerned region setting unit and the channel collimator make it possible to execute the photography in such a manner that the X-ray irradiation toward a region other than the concerned region is suppressed up to the smallest possible degree. Moreover, an image in the region outside of the concerned region is reconstructed by fitting and embedding previously measured data and so on.

As is obvious from the above-described detailed explanation, according to the X-ray CT in the present invention, in operations such as re-inspection and a CT fluoroscopic photography, it is possible to reduce ineffective and needless X-ray exposure by employing local measurement scanning. In the local measurement scanning, only a range obtained by restricting in advance a portion to be photographed (a concerned region) is irradiated with X-rays. Also, as to data in a region other than the concerned region, embedding of data that are previous in time makes it possible to reconstruct an image with fewer artifacts. Namely, these characteristics make it possible to obtain, with a low X-ray exposure dose and concerning the image outside of the concerned region as well, a precise and high picture quality image that has a relatively small difference in time.

In addition, the present invention makes it possible to reduce the X-ray exposure dose toward a subject or the operator without decreasing the tube electric current. This characteristic permits a high accuracy diagnosis or operation to be performed without deteriorating picture quality of the image. Also, regarding the boundary between the inside and the outside of the concerned region, the boundary has been indicated clearly on the image. This is a measure to be taken to prevent a misdiagnosis.

BEST MODE FOR CARRYING OUT THE INVENTION

Using the accompanying drawings, the detailed explanation will be given below concerning embodiments in the present invention.

Figure 1:
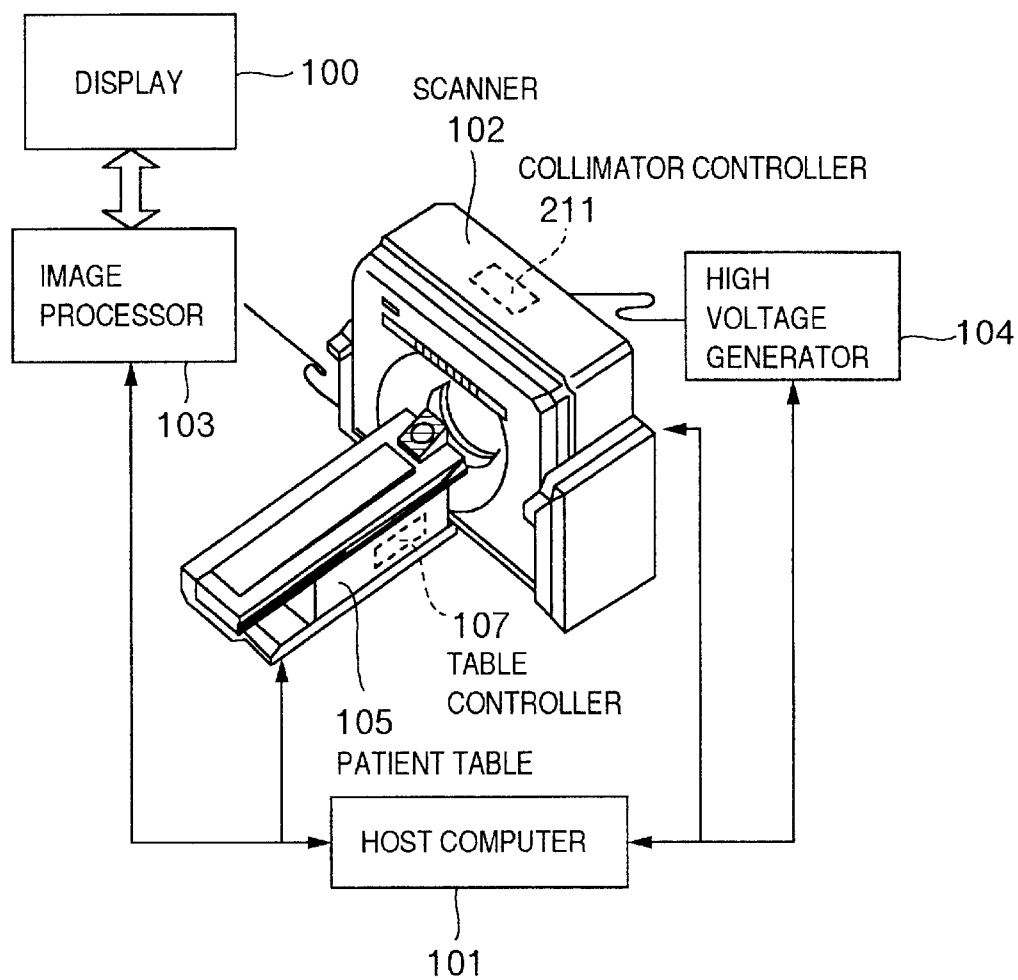
FIG. 1 is an entire configuration diagram of an X-ray CT in the present invention.

First, FIG. 1 shows an entire configuration of an X-ray CT according to an embodiment in the present invention. As is apparent from the drawing, the X-ray CT includes a display 100, a host computer 101 for controlling the entire apparatus, a scanner system 102 mounting thereon systems such as an X-ray generating system and an X-ray detecting system and allowing a continuous scanning with the use of a slip ring, an image processor 103 being in charge of a pre-processing of an image, an image reconstructing processing or various kinds of analyzing processings and including a preamplifier (indicated by reference numeral 106 in FIG. 2), a high voltage generator 104 for feeding a high voltage to the X-ray generating system, a patient table 105 for mounting a subject thereon, a table controller 107 for controlling a position in x, y, z directions of the patient table 105, a slice collimator (108 in FIG. 2) for restricting X-ray irradiation range to a slice width, a channel collimator (210 in FIG. 2) for restricting X-ray irradiation range in a fan beam direction, a collimator controller 211 for controlling a convergence position of the channel collimator, and so on. Incidentally, although not illustrated, the host computer 101 includes as its input apparatuses a keyboard, a mouse, a tracking ball, and so on.

Figure 2:
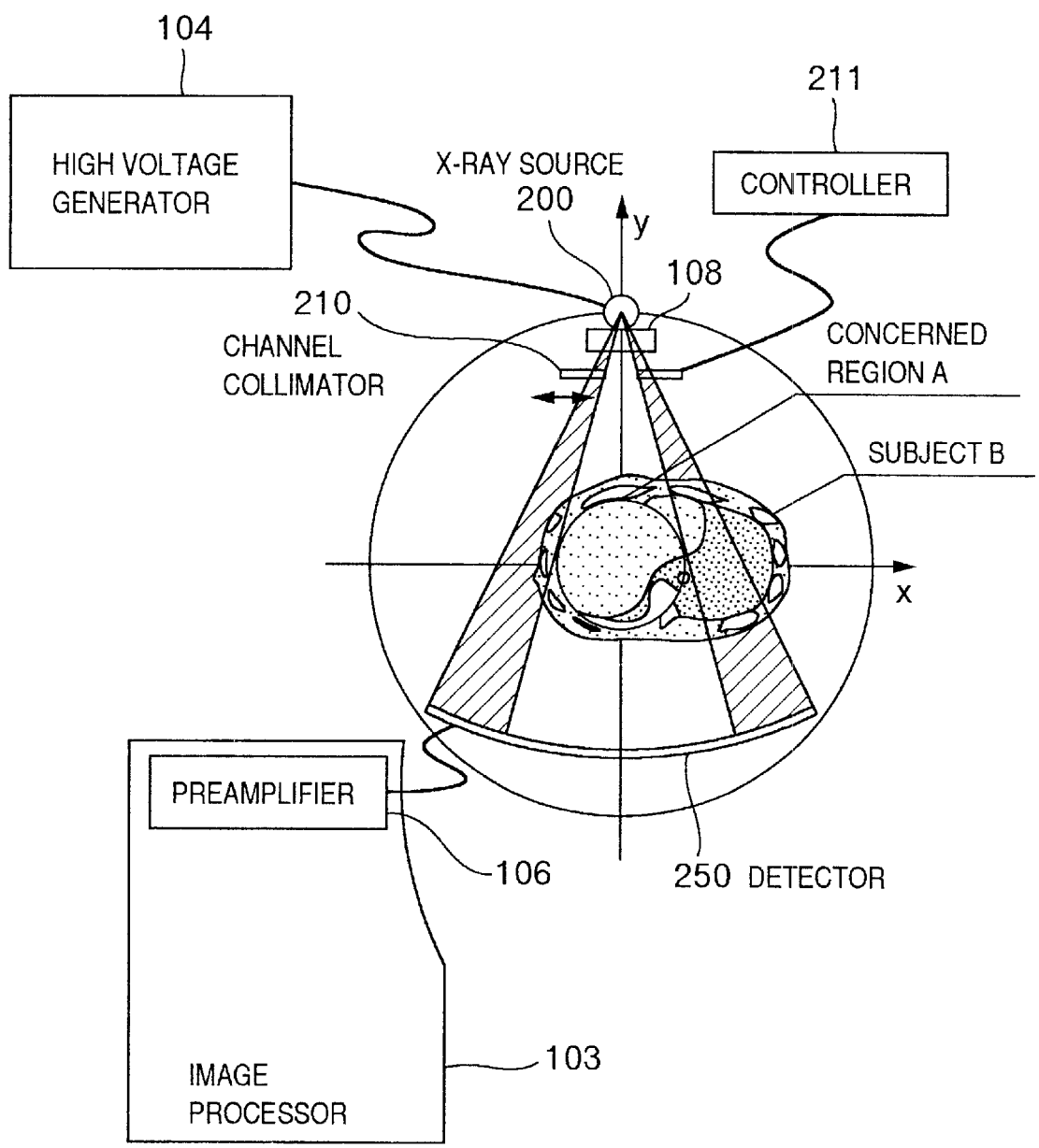
FIG. 2 is a detailed illustrative diagram of a scanner system in the X-ray CT in the present invention.

FIG. 2 is a detailed illustrative diagram of the above-mentioned scanner system 102. According to the configuration of the X-ray CT in the present invention, in proximity to an X-ray tube (an X-ray source) 200 and at the same time between the X-ray tube and a subject B to be inspected, the channel collimator 210 is installed. The X-ray tube generates an X-ray with the use of the high voltage fed from the high voltage generator 104. Moreover, the channel collimator 210 is controlled by the collimator controller 211 in such a manner as to move in an x direction as shown in the drawing. Namely, the channel collimator 210 is configured so that it can restrict X-ray irradiation range in a channel direction to a concerned region A that is settable in advance. Also, reference numeral 250 in the drawing denotes the X-ray detecting system in the scanner system 102.

In addition to the channel collimator 211, there is provided the slice collimator 108. The slice collimator is a collimator for determining a slice width and thus it differs from the channel collimator. In general, both of the collimators are used in combination.

Figure 3A:
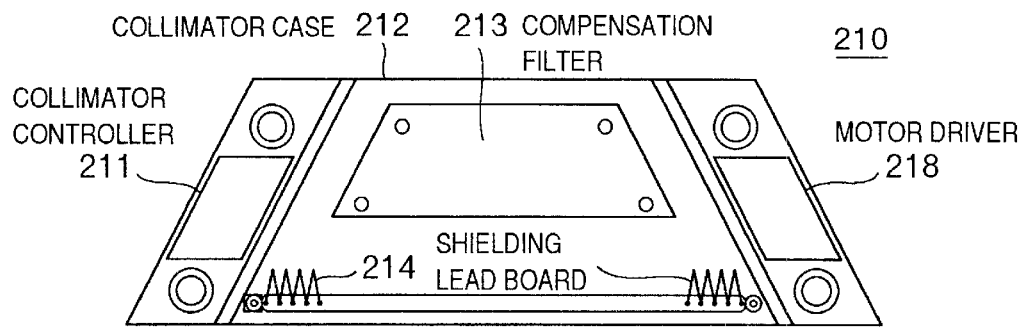
FIGS. 3A, 3B are detailed illustrative diagrams of a channel collimator in the present invention.
Figure 3B:
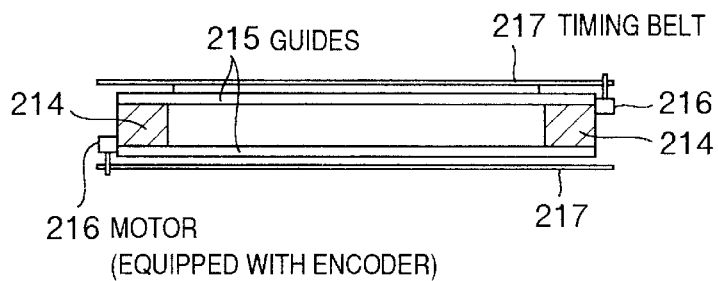
Figure 4A:
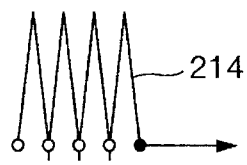
FIGS. 4A, 4B are diagrams illustrating operation of a shielding lead board in the channel collimator.
Figure 4B:
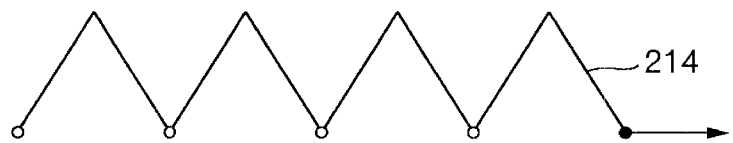

Next, FIGS. 3A, 3B and FIGS. 4A, 4B illustrate a schematic structure of the channel collimator 210 that characterizes the present invention. As is illustrated in FIG. 3A, the channel collimator 210 includes a compensation filter 213 inside a collimator case 212 that is trapezoid-shaped in the outside appearance, and also includes a shielding lead board 214 at the base portion thereof. Also, FIG. 3B shows the structure of a lower surface portion of the channel collimator 210. Pair of guides 215 are provided on the both sides of the above-described shielding lead board 214. Extension or contraction of the shielding lead board 214 is controlled by working operations of a motor 216 equipped with devices such as an encoder and a timing belt 217. Incidentally, FIG. 4A and FIG. 4B show a state where the shielding lead board 214 is contracted and a state where it is extended, respectively.

Also, as is illustrated in the above-mentioned drawing, the collimator case 212 is further provided with the collimator controller 211 directing and controlling the whole channel collimator 210 and a motor driver 218 driving the above-mentioned motor 216. The collimator controller 211 and the motor driver 218 may be installed on a member other than the collimator case 212.

Speaking of the above-described collimator controller 211, at the time of, for example, setting the concerned region A in the present invention, as its first step, several types of tables are stored in the collimator controller. Also, the above-described motor driver 218 drives and rotates the motor 216. Then, the rotation of the motor is transmitted to the timing belt 217. This allows the timing belt 217 to cause the curtain-shaped shielding lead board 214 to be extended or contracted. This extension or contraction makes it possible to carry out the scanning of the concerned region during the scanning as a whole.

Additionally, FIGS. 3A, 3B, 4A, and 4B illustrate just one example, and, naturally, there can be the other structure of the channel collimator and the other controlling mechanism therefor.

Figure 5A:
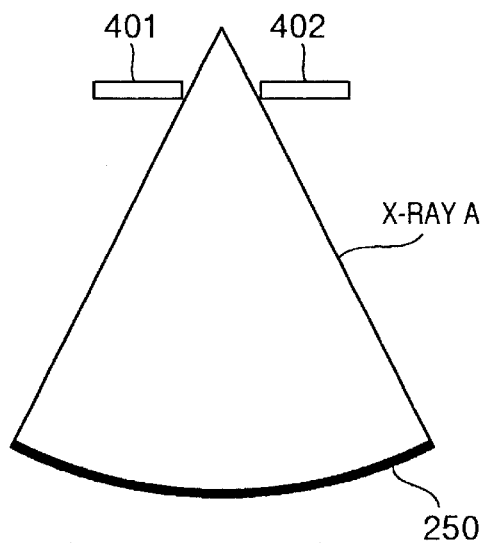
FIGS. 5A to 5C are diagrams showing a relation between a convergence position of the channel collimator and X-ray irradiation.
Figure 5B:
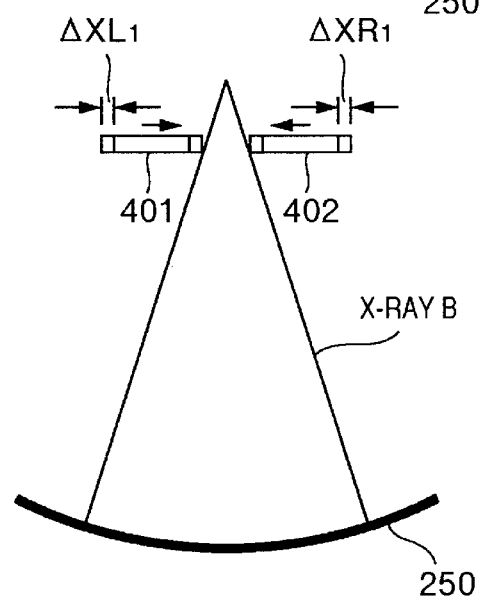
Figure 5C:
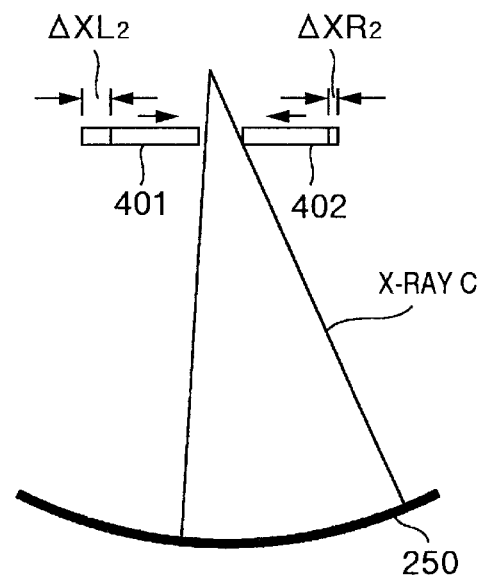

FIGS. 5A to 5C show a relation among collimators 401, 402, X-ray fan beams, and the detector 250.

FIG. 5A shows a position relationship among the collimators 401, 402 (which correspond to the shielding lead board 214 in FIG. 3A) for the original and normal CT measurement, i.e. the global measurement scanning, an X-ray fan beam A, and the detector 250. Meanwhile, FIG. 5B shows a position relationship among the collimators 401, 402 for a CT measurement at a certain view angle (a projection angle), an X-ray fan beam B, and the detector 250. Moreover, FIG. 5C shows a state at another view angle. In FIG. 5A, the collimators 401, 402 are in their reference positions. Meanwhile, FIG. 5B shows an example where the collimator 401 is displaced to the right by $\Delta XL_1$, and the collimator 402 is displaced to the left by $\Delta XR_1$. Moreover, FIG. 5C shows an example where the collimator 401 is displaced to the right by $\Delta XL_2$ and the collimator 402 is displaced to the left by $\Delta XR_2$. In the present invention, displacement data $\Delta XL_j$, $\Delta XR_j$ for each view j are stored as a table in the memory, and then the displacement data are read out for each view angle so as to achieve the position control.

Here, using FIG. 6, the explanation will be given below concerning the control of the channel collimator 210.

Figure 6:
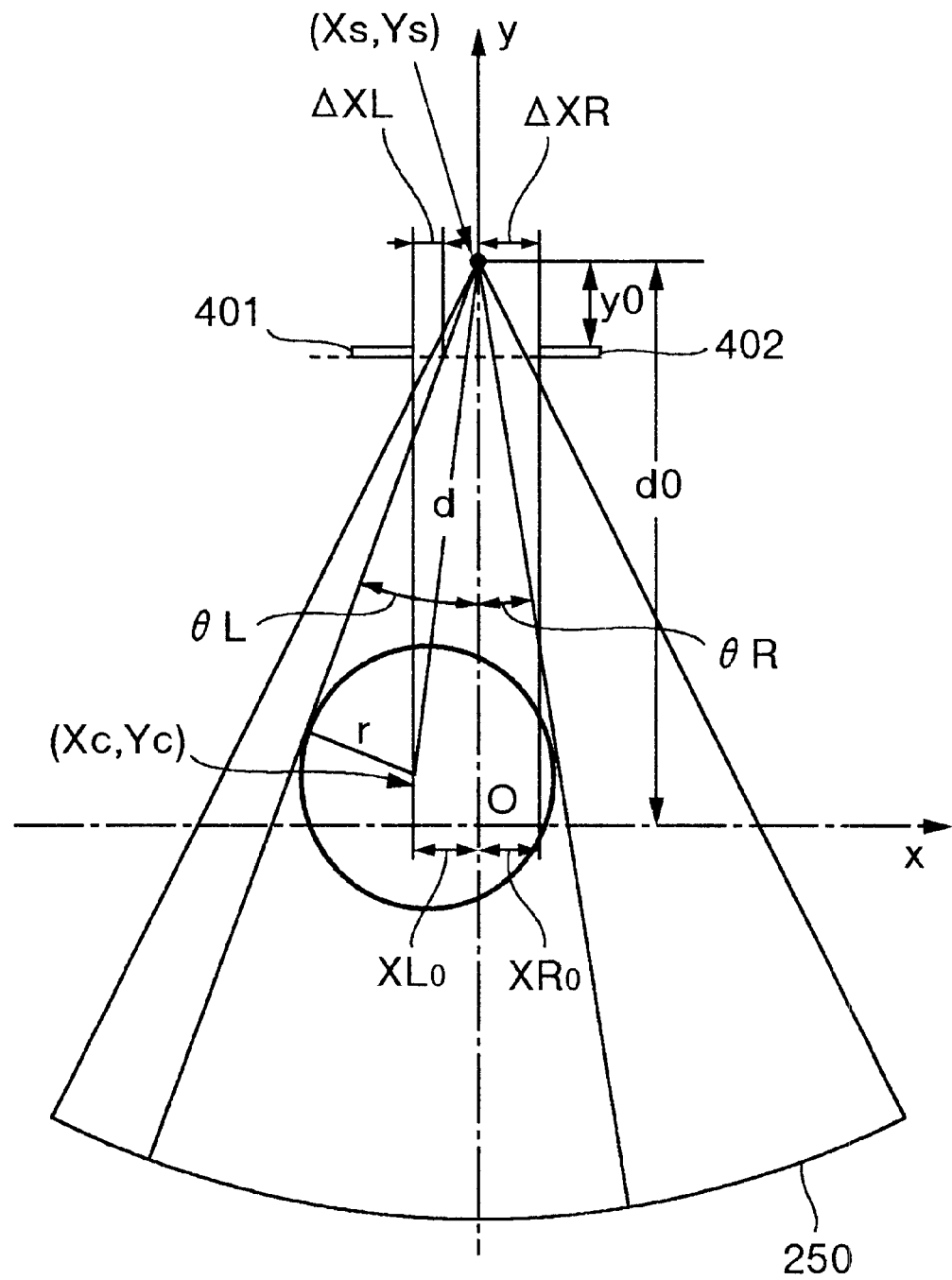
FIG. 6 is a geometrically illustrative diagram of the channel collimator.

First, as is illustrated in FIG. 6, a straight line, which is drawn from a focal point position (Xs, Ys) of the X-ray tube, i.e. the generating source of an X-ray, to a center of rotation O of the X-ray tube, is taken as a y axis, and a straight line that intersects the y axis at right angles at the center of rotation O is taken as an x axis.

Here, the mechanism of the collimators 401, 402 is such that they are movable in the x direction as described earlier, thereby, as is also illustrated in FIGS. 5A to 5C, making it possible to arbitrarily restrict the X-ray irradiation range for each view.

Now, in FIG. 6, assuming that the concerned region is defined by a circle with its center as a central coordinate (Xc, Yc) and having a radius r, it turns out that the X-ray irradiation range thus set ranges from θL to θR as an angle of viewing the focal point in perspective. Accordingly, displacement amounts of the collimators 401, 402 from normal positions on the x axis become $\Delta XL$, $\Delta XR$ in the drawing. Here, the normal position of the collimators 401, 402 are defined as $XL_0$, $XR_0$, while a coordinate of the focal point of the X-ray is defined as (Xs, Ys), considering the focal point to be a point focal point as described above. Then, it turns out that a position coordinate of the collimators 401, 402 ($XL_0-\Delta XL$, $XR_0-\Delta XR$) varies, depending on each projection angle.

Incidentally, speaking of means of determining $\Delta XL$, $\Delta XR$, i.e. the displacement amounts of the collimators 401, 402 from the normal positions, $\Delta XL$, $\Delta XR$ can be obtained by the following calculating formulae and thus let's determine them beforehand here. Also, instead of using the following calculating formulae, it is possible to make the approximations using periodic functions such as trigonometric functions.

Namely, $\Delta XL$, $\Delta XR$ are determined in the following way:

$$d = \sqrt{(Xs - Xc)^2 - (Ys - Yc)^2} \tag{1}$$

Here, d is an inter-two point distance between the focal point and the central coordinate of the concerned region. Representing θL and θR with the use of d, the resultant formulae are as follows:

$$\theta L = \sin^{-1}\frac{r}{d} - \tan^{-1}\frac{Xc}{d_0 - Yc} \tag{2}$$

$$\theta R = \sin^{-1}\frac{r}{d} + \tan^{-1}\frac{Xc}{d_0 - Yc} \tag{3}$$

Wherein $d_0$ is a distance between the focal point of the X-ray and a center of rotation of the scanner. Representing $\Delta XL$, $\Delta XR$ with the use of θL and θR, the resultant formulae are as follows:

$$\Delta XL = XL0 - y0\tan\theta L \tag{4}$$

$$\Delta XR = XR0 - y0\tan\theta R \tag{5}$$

Figure 7:
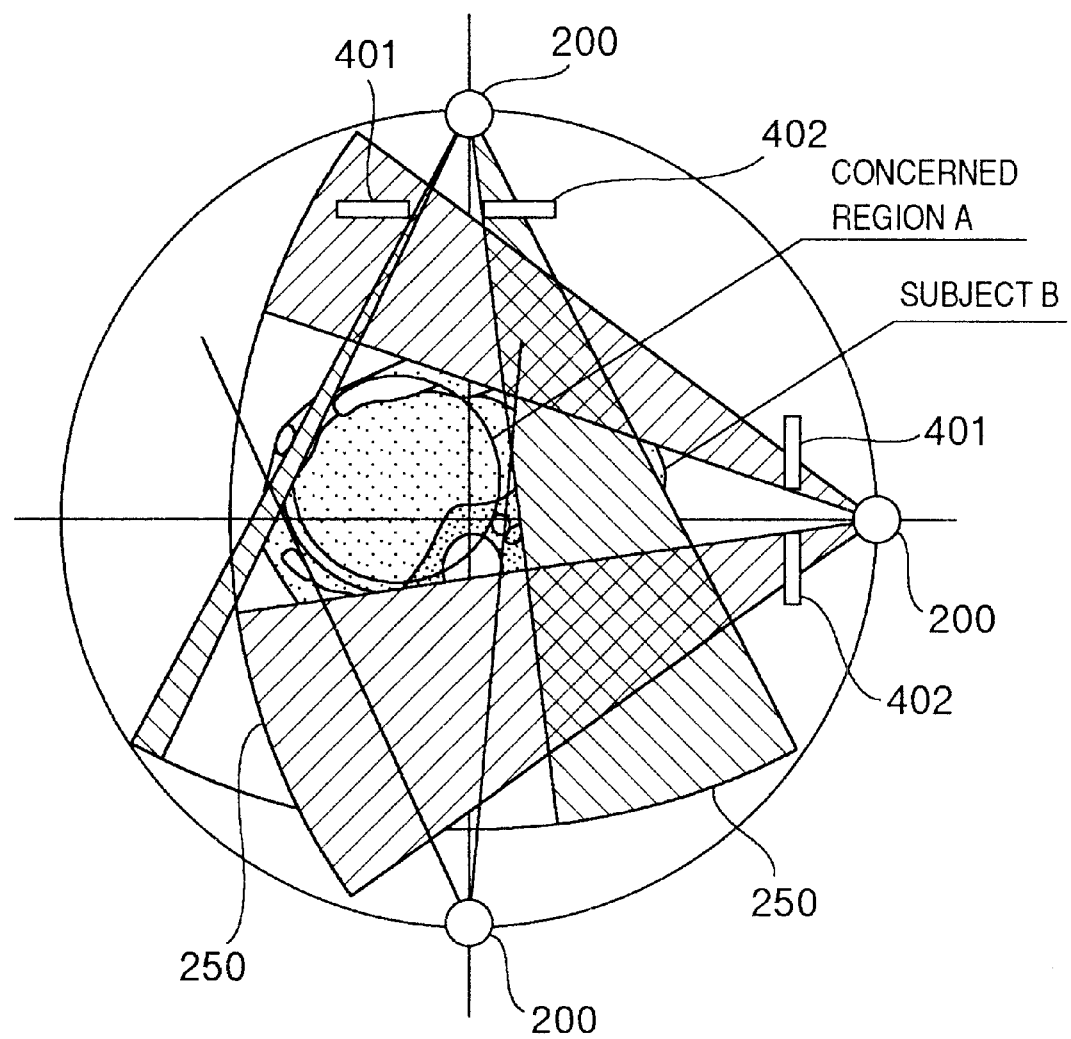
FIG. 7 is a diagram illustrating scanning of a concerned region by the X-ray CT in the present invention.

In accordance with $\Delta XL$, $\Delta XR$ determined above, positions of the channel collimators 401, 402 are controlled for each projection angle. This, as is illustrated in FIG. 7, permits only the concerned region A of the subject to be inspected to be irradiated with X-rays. Incidentally, although, in the above-mentioned example, the explanation has been given assuming that the concerned region is the circle, the configuration of the concerned region is not limited to a circle. It may be the other configuration such as, for example, an ellipse. In that case, parameters are added to the below-described procedures of determining $\Delta XL$, $\Delta XR$.

If the above-described movements of the collimators are carried out continuously, i.e. the collimators move during one view measurement as well, there are actually some cases where edge of the X-ray irradiation range does not completely coincide with boundary of a detecting element in the detector 250 at the time of measuring each projection data. However, since a method described later makes it possible to decide an effective channel, accuracy of the displacement amounts of the collimators need not be so high. Depending on the cases, it is possible to make approximations of the controlling parameters using periodic functions such as a sinusoidal wave.

Figure 8:
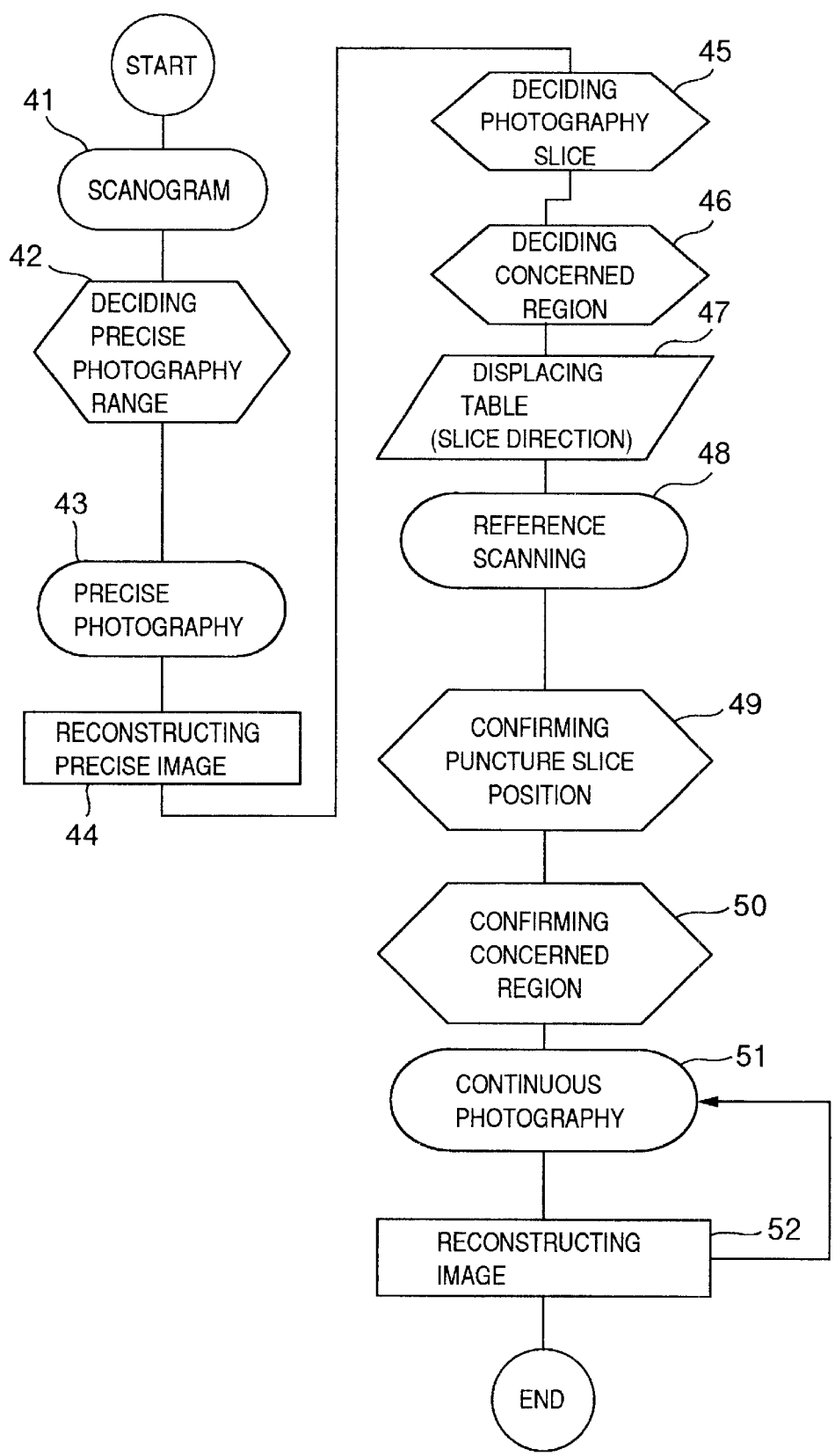
FIG. 8 is a diagram showing an embodiment of flow of the photography in the X-ray CT in the present invention.

Next, the explanation will be given below concerning flow of the photography in the X-ray CT the configuration of which has been explained above. Incidentally, when a portion that the operator wishes to photograph is recognized in advance, the X-ray CT in the present invention is usable for, for example, reinspection after the operation, biopsy of a tumor through the CT fluoroscopy, and so on. The photography procedure will be explained below, using FIG. 8. Namely, in the photography procedure, only a concerned region, i.e. the portion that the operator wishes to photograph, is irradiated with X-rays, thereby embodying lowering of the X-ray exposure dose in the X-ray CT.

Referring to the flow of the photography, when the photography is started, a scanogram (a fluoroscopic image that is photographed with the X-ray tube at rest and with the patient table 105 being moved) is displayed first (step 41), and next a decision on a precise photography range is made (step 42).

In the decision on a precise photography range, after setting the patient on the table 105 is over, in order to decide a photography position of the tomographic image, the above-described scanogram is obtained first. Moreover, setting the number of the photographs is performed on the displayed scanogram. The photography range is an item related to items such as a photography starting, a photography interval and the number of the photographs. For example, in the case of helical scanning, items such as the photography starting position, a table-moving speed and the number of the scanning are also set.

After that, a precise photography is executed (step 43). In the precise photography, in accordance with the conditions set above, the host computer 101, for example, sets a tube electric voltage and a tube electric current to the high voltage generator 104, and also sets to the table controller 107 a moving speed at the time of the helical scanning and so on. At the time of the precise photography, the above-described channel collimators 210, 401, 402 are in their normal positions, and thus the X-ray is let into all the channels. This permits a sufficiently diagnostic image to be obtained in the subsequent reconstruction of a precise image (step 44).

Subsequently, a decision on a photography slice (step 45) and a decision on a concerned region (step 46) are executed. Namely, when the above-described precise photography is finished, in the photography slice, the operator observes the photographed image and, in the case of, for example, the reinspection and so on, selects a slice suitable for a portion that he or she wishes to observe most. Also, in the case of the CT fluoroscopy, the operator obtains information on the periphery of a target tissue (a tumor), such as a position of the target tissue or whether or not there exists an important tissue on a puncture route up to the target tissue, and decides a puncture slice at the time of the CT fluoroscopy. Furthermore, in the decision on a concerned region, the operator sets a range to be irradiated with X-rays on the slice decided above, i.e. the concerned region A. Additionally, as is illustrated in, for example, FIG. 9, the setting of the concerned region is carried out by describing, for example, a circular region or an elliptic region on a display screen of the display 100, using pointing devices such as a mouse and a tracking ball as input apparatuses. At the same time, X-ray irradiation toward outside the set concerned region is suppressed up to the smallest possible degree. In addition, the table is displaced in the slice direction up to the set photography slice position (step 47).

Next, in a reference scanning (step 48), the data are measured one time under the same conditions as those in a continuous photography to be performed thereafter. Namely, in the reference scanning, following an instruction by the host computer 101, the table controller 107 displaces the table up to the selected slice position. Then, with an X-ray dose that is appropriate for a photography purpose of the CT fluoroscopy such as the re-inspection or the puncture, the photography where the channel collimator 210 is in its normal position (the global measurement scanning) is executed.

Next, in a puncture slice position-confirming step 49, it is confirmed whether or not the target tissue is contained within the slice. In a concerned region-confirming step 50, by actually displacing the channel collimators, it is confirmed whether or not the image in the concerned region has been displayed in a good condition.

If a desired image is obtained by the reference scanning, while controlling positions of the channel collimators 401, 402 so that the positions thereof become the irradiation field of view (range), go to the continuous scanning of puncture photography (step 51). Then, the photography data are reconstructed sequentially so as to display a tomographic image that is continuous in time (step 52).

Subsequently, the explanation will be given below concerning an image reconstruction based on projection data obtained by irradiating only the concerned region with X-rays.

In an image reconstruction, it is often requested to reconstruct an image in a region outside the concerned region. The explanation will be given below concerning an example of the processing content for the reconstruction.

Figure 10:
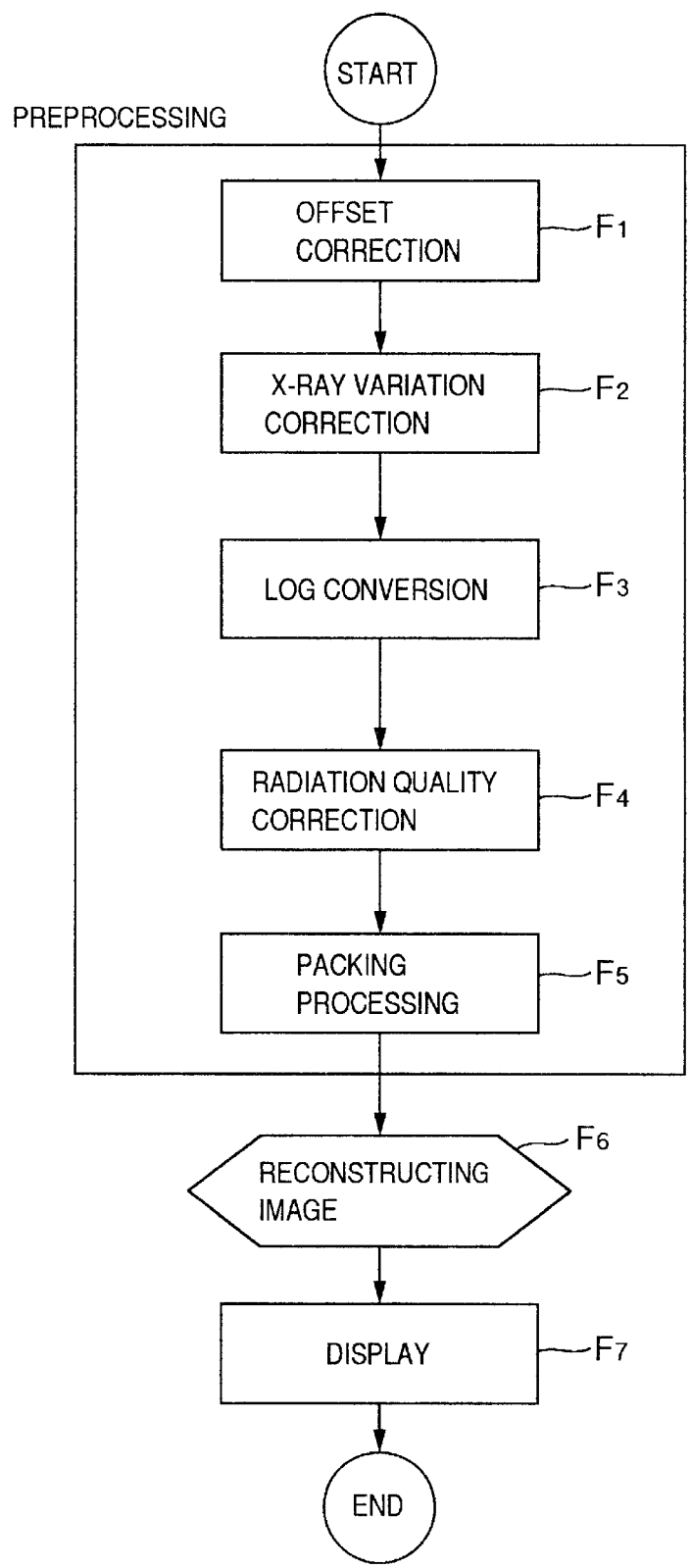
FIG. 10 is a diagram explaining flow of image reconstruction according to the present invention.

FIG. 10 shows the flow chart thereof. In FIG. 10, an offset correction by a preamplifier dark current (F1), an X-ray variation correction (F2), and a packing processing (F5) as preprocessing for a log conversion and a radiation quality correction (F3, E4) are added. After that, the image reconstruction is executed (F6), and then the image thus reconstructed is displayed (F7). Here, the packing processing means a processing in which a data range that is ineffective for the reconstruction is restricted is determined and the data therein are replaced by previously measured data, since the irradiation range is restricted.

Figure 11A:
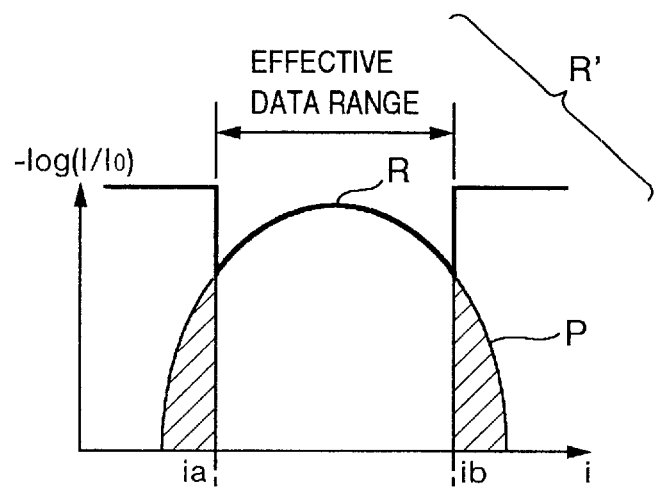
FIGS. 11A to 11C are diagrams explaining data embedding in the present invention.
Figure 11B:
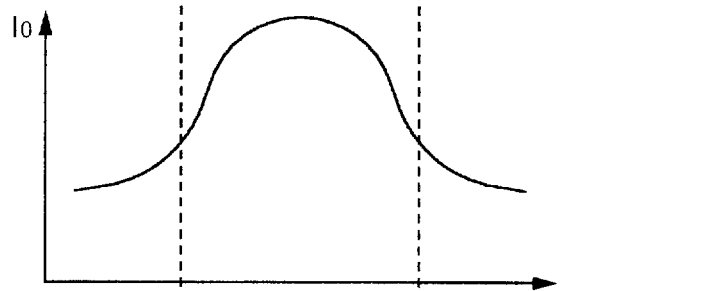
Figure 11C:
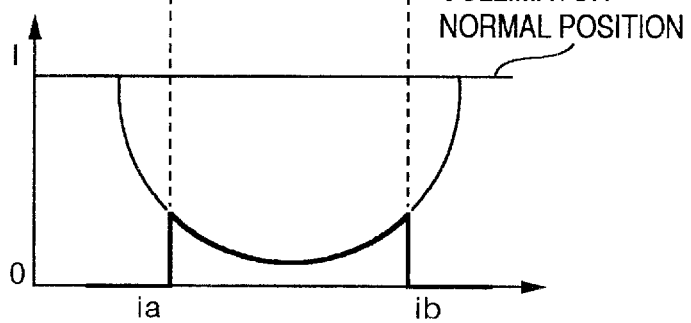

Then, using FIGS. 11A to 11C, the explanation will be given below concerning projection data that are measured when the photography is performed with the irradiation range restricted. FIG. 11B shows an output $I_0$ at each position of the detector in a state where there is no subject to be photographed, i.e. in the case of photographing air. Positions of the channel collimators correspond to ia, ib. FIG. 11C shows a detector output I at the time of performing the photography with a subject to be photographed inserted. FIG. 11A shows an output after the log conversion. As is indicated by a bold solid line in FIG. 11C, projection data in a range shielded by the channel collimators 401, 402 become equal to substantially zero after the offset correction. Consequently, at the time of data calculation after the log conversion illustrated in FIG. 11A, since $I/I_0$ is an extremely small value, an overflow takes place. At this time, if data outside the effective data range of the projection data after the log conversion are set to be zero, extremely high frequency components occur at the boundary channels ia, ib, and are emphasized by a reconstructing filter. This causes artifacts to appear on the image. The measure for solving these problems is the packing processing.

The boundary channels ia, ib can be determined easily by θL, θR of the formulae (2), (3). However, a reliability of the data in proximity to the boundary channels is rather low, because, as described earlier, the edge of the X-ray irradiation range does not completely coincide with the boundary of the detecting element and the reliability depends on the displacement accuracy of the collimators. Accordingly, it may be possible to employ, a method of regarding inside data by several channels as effective considering a little margin. Otherwise, it is also advisable to define ia, ib by performing a threshold processing toward the data after the offset correction in FIG. 11C. The use of the threshold processing makes it possible to easily determine the effective data range even if the displacement accuracy of the collimators is somewhat low.

After the effective data range has been decided, a processing is executed that fits data existing in an ineffective data range of data obtained by the global measurement scanning. Here, the data obtained by the global measurement scanning mean data measured previously with no collimate in the channel direction (data measured at the positions of the collimators 401, 402 on the regular CT measurement).

Assuming that, in FIG. 11A, projection data to be processed are R (i, j) and previously measured projection data are P (i, j) (i.e., for example, projection data measured with no restriction by the channel collimators at the time of the puncture slice position-confirming scanning), projection data after the packing processing R' (i, j) are given by the following formula. Reconstruction of R' (i, j) allows an image of the concerned region to be obtained. Here, reference note i denotes channel number and j denotes projection number.

$$R'(i, j) = \begin{cases} P(i, j) & i \leq ia, i \geq ib \\ R(i, j) & ia < i < ib \end{cases} \quad (6)$$

The packing processing presents no problem in the case of completely identical slices. If the slices are shifted, however, it is considered that a difference in level is formed at joints between the two projection data, i.e. P and R. In the case where there occur such non-negligible difference in level, it is necessary to perform processings such as a moving average or a weighted average toward data in proximity to the joints so that the two projection data are connected smoothly to each other.

Figure 12:
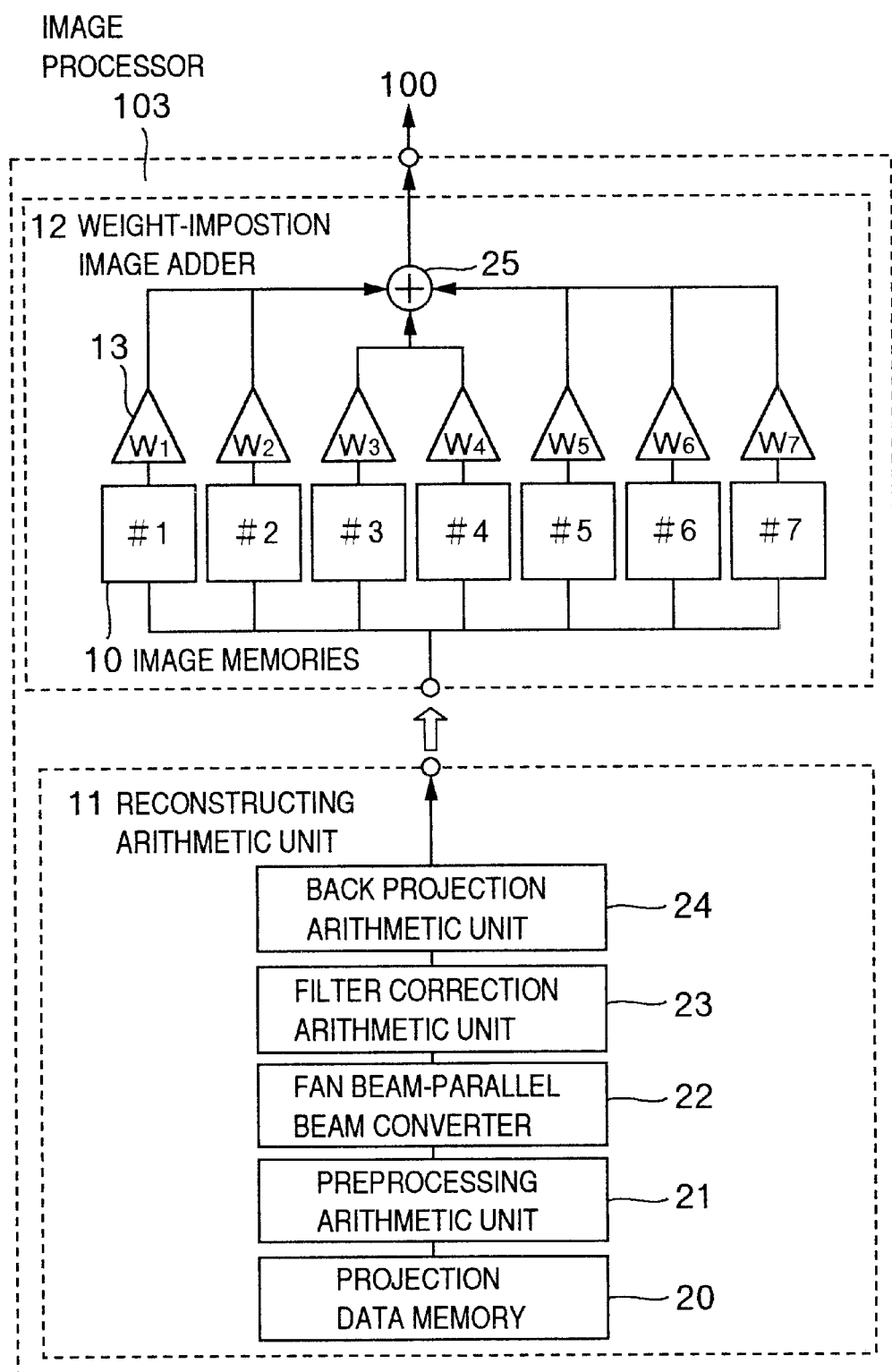
FIG. 12 is a block diagram illustrating an example of an image processor in the X-ray CT in the present invention.

FIG. 12 shows an embodiment in which a processing is executed that embeds the previously measured projection data toward the projection data in the range shielded by the channel collimators.

In FIG. 12, the image processor 103, which includes a reconstructing arithmetic unit 11 and a weight-imposition image adder 12, produces an output to the display 100. Moreover, the reconstructing arithmetic unit 11 includes a projection data memory 20, a preprocessing arithmetic unit 21, a fan beam-parallel beam converter 22, a filter correction arithmetic unit 23, and a back projection arithmetic unit 24. The weight-imposition image adder 12 includes seven units of image memories 10 (#1 to #7), seven units of weight coefficient multipliers 13 (reference notations $W_1$ to $W_7$ denote weight coefficients), and an adder 25.

Incidentally, the image processor 103 is configured so that, when a scanning rotation is a 1-second-per-rotation, the image processor is capable of reconstructing one image in, for example, less than one second. In this case, partially reconstructed images are obtained in a width of, for example, 30° one after another sequentially, and one reconstructed image can be obtained by adding a plurality of latest partially reconstructed images. Accordingly, in the 30° width of angle updating, 12-images-per-scond of reconstructed images can be obtained.

Also, the reconstructing arithmetic unit 11 obtains the reconstructed image by performing a preprocessing made by the arithmetic unit 21, a conversion to a parallel beam made by the fan beam-parallel beam converter 22, a filter correction processing made by the arithmetic unit 23, and in addition a back projection arithmetic operation made by the back projection arithmetic unit 24. This reconstructing arithmetic operation is not a 360° amount of batch-type reconstructing arithmetic operation but an adding arithmetic operation of the partially reconstructed images obtained from parallel beam data in a width of a partial angle (for example, in the width of 30°)

Furthermore, the weight-imposition image adder 12 allots one by one, to each of the image memories 10, i.e. #1 to #7, the partially reconstructed images obtained one after another by the reconstructing arithmetic unit 11. For example, a partially reconstructed image $g_1$ is allotted to #1, a partially reconstructed image $g_2$ is allotted to #2, . . . , and a partially reconstructed image $g_7$ is allotted to #7, and then the partially reconstructed images are stored. Concerning the remainder, i.e. partially reconstructed images $g_8$, $g_9$ . . . , the allotment is carried out in such a manner that $g_8$ is allotted to #1 instead of $g_1$, $g_9$ is allotted to #2 instead of $g_2$, . . . , and then the storing is executed.

Making the weight coefficients, $W_1$ to $W_7$, correspond to the partially reconstructed images stored in the memories #1 to #7, respectively, the weight coefficient multipliers 13 multiply each of the images by each of the weight coefficients, thus performing a weight-imposition onto each of the partially reconstructed images. The adder 25 executes a total addition thereof, thereby obtaining one reconstructed image.

Figure 13A:
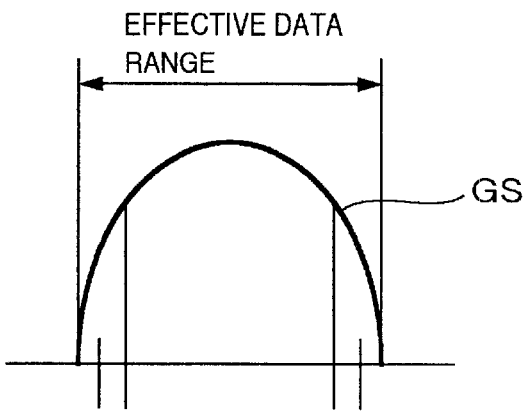
FIGS. 13A to 13C are diagrams explaining an example of a correcting method for data outside the concerned region.
Figure 13B:
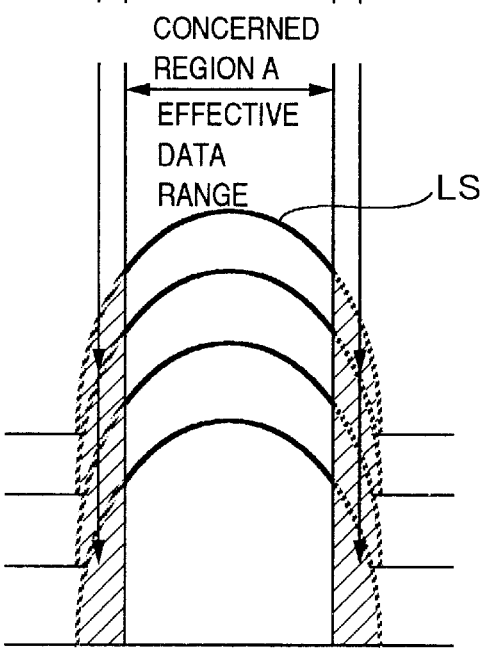
Figure 13C:
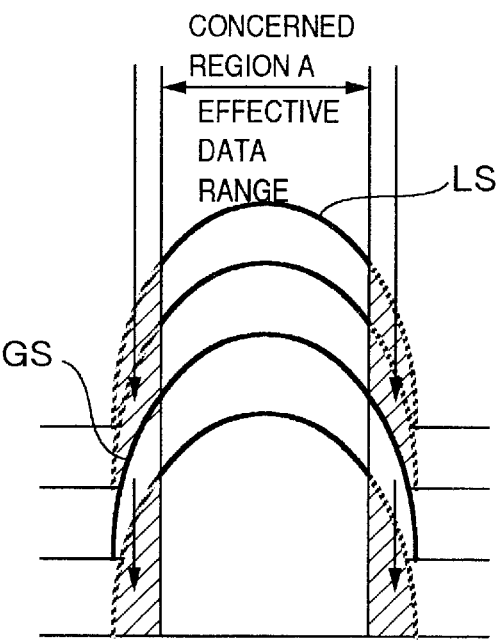

FIGS. 13A to 13C show the concept of the above-described image reconstruction processing performed by the image processor 103. Namely, the effective data range obtained by the global measurement scanning (GS) proves to be the range indicated by GS in a bold solid line in FIG. 13A. In contrast to this, the projection data obtained by the local measurement scanning (LS) in the present invention, in which the X-ray irradiation is executed with the X-ray restricted only to the concerned region, prove to be the data illustrated in FIG. 13B in the case of a continues scanning, such as the helical scanning and a dynamic scanning, or in the case of repeating the CT fluoroscopy and so on. As is seen from LS in FIG. 13B, image data outside the concerned region A are discontinuous in time or in space, thus scarcely allowing high picture quality to be accomplished.

Then, as illustrated in FIG. 13C, in the course of the above-described continuous scanning or CT fluoroscopy, a scanning GS (global measurement scanning) where the channel collimator 210 is in its normal position is executed. Moreover, at the time of a continues local measurement scanning LS before or after this scanning, projection data obtained by a global measurement scanning that is the nearest thereto in time are embedded as correction data toward regions outside the concerned region A. This transaction is capable of embodying an image reconstruction processing that makes possible lowering of the X-ray exposure dose and accomplishing of the high picture quality toward the regions outside the concerned region A as well. Namely, this makes it possible to obtain, with a low X-ray exposure dose, images that have a small difference in time between the regions inside and outside the concerned region A, thereby obtaining the image that is easier to see.

Figure 14:
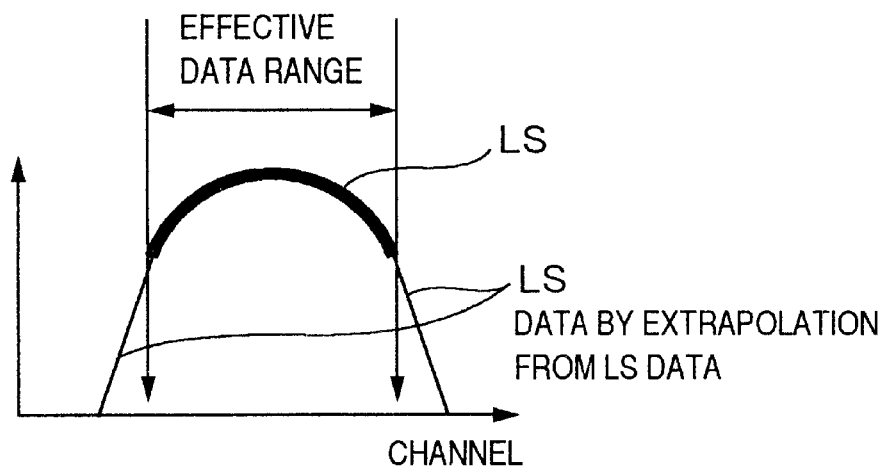
FIG. 14 is a diagram explaining another example of the correcting method for the data outside the concerned region.

The above-stated explanation is about the case where the GS data can exist. In the case where there exist no Gs data, it is possible to correspond through extrapolation of the outside the concerned region from the data inside the concerned region. FIG. 14 presents the explanation thereof. As the extrapolation, simple least-squares method may be used, or a higher order interpolation such as Newton interpolation may be used.

In the case where the extrapolation is used, the discontinuous image data can also be avoided similarly in the case where the GS data is used.

When the subject extends off width of the detector, the extrapolation can be used for reconstructing an image of the portion of the subject that extends off.

Also, as described earlier, the image outside the concerned region A is a high picture quality image (i.e. the projection data obtained by the global measurement scanning that is the nearest thereto in time) with a difference in time eliminated up to the smallest possible degree.

Nevertheless, not a little difference in time exists between the image outside the concerned region A and the image inside the concerned region A. On account of this, when applying the present invention to the continues scanning or the CT fluoroscopy, the operator is likely to mistake the image outside the concerned region A for the image inside the concerned region A. It cannot be denied that this may result in his misdiagnosis.

Figure 9:
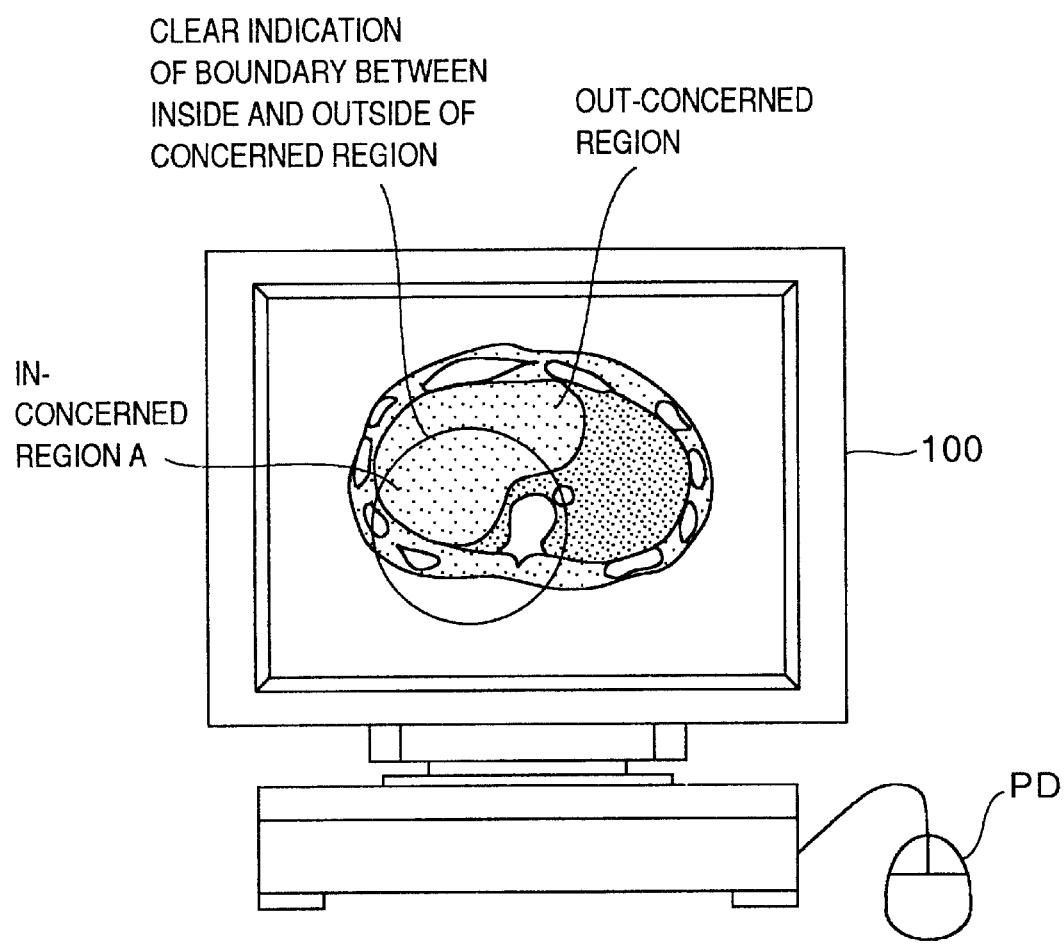
FIG. 9 is a diagram showing an embodiment clearly indicating a boundary of the concerned region.

Then, in the present invention, as a measure of clearly indicating a boundary between the inside and the outside of the concerned region A, as illustrated in FIG. 9, the boundary line BL between the inside and the outside of the concerned region A has been indicated clearly on the displayed image of the display 100, thereby preventing the above-mentioned mistake and misdiagnosis. As the measure of clearly indicating the boundary line BL, the following are appropriate: The boundary line (a circle in FIG. 9) surrounding the concerned region A is described with a line that, including a meaning of warning, is of a conspicuous color such as, for example, red. Otherwise, in the case of a black-and-white monitor, a black or white line is used, or is blinked thereby allowing the observer to recognize the boundary line easily.

Figure 15:
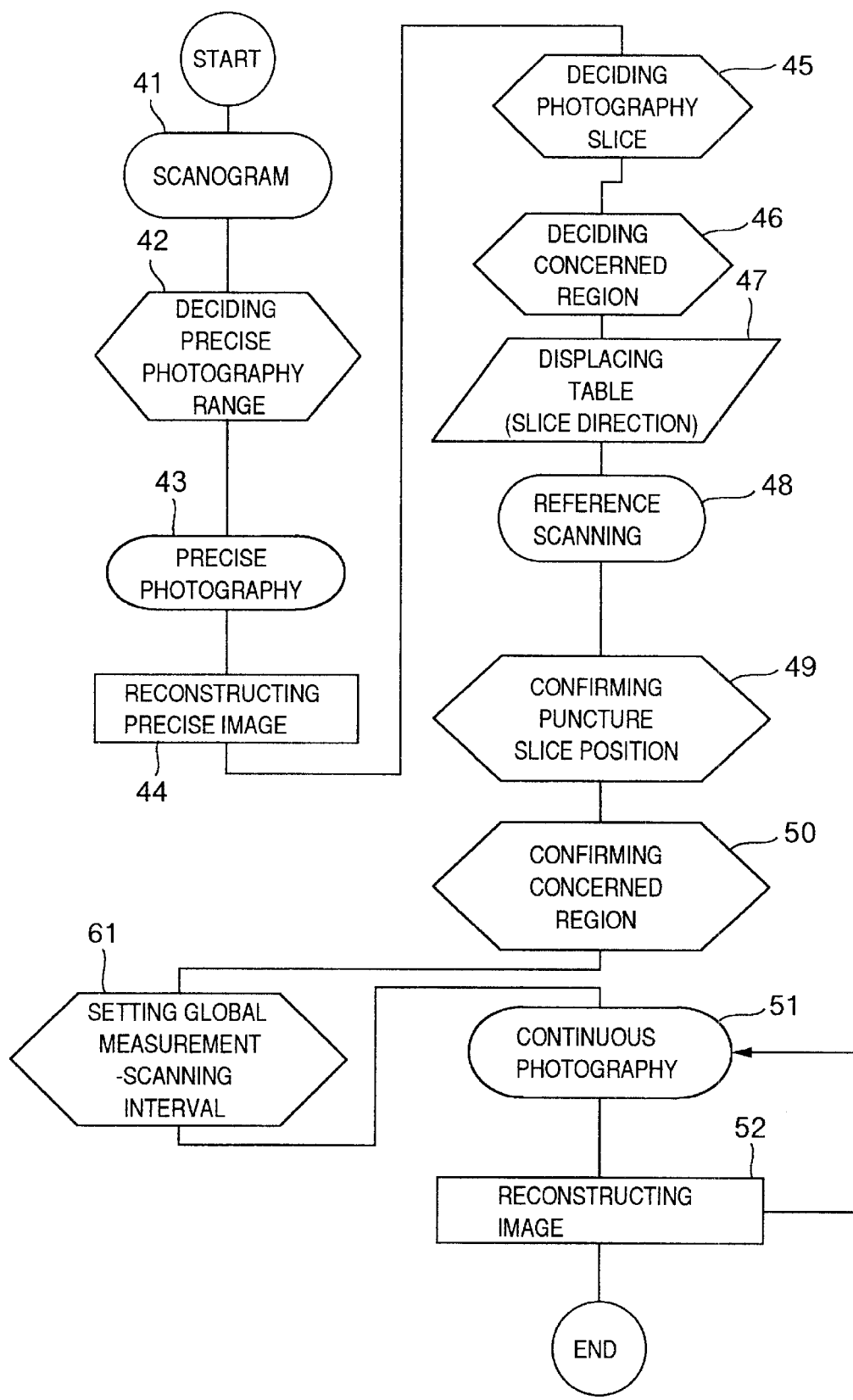
FIG. 15 is a diagram showing another embodiment of the flow of the photography in the X-ray CT in the present invention.

FIG. 15 shows an embodiment of flow of the photography in which the global measurement scanning is executed in the course of the local measurement scanning. The steps other than a setting of a global measurement-scanning interval (step 61) are the same as the steps in the flow illustrated in FIG. 8, and accordingly the explanation thereof is omitted.

In the setting of the global measurement-scanning interval at step 61, before proceeding to the continuous photography and so on, it is set how many times the photography where the channel collimator 210 is in its normal position is executed in the course of the continuous photography. Incidentally, here, the more minutely the setting is made, the smaller the shift in time of the image outside the concerned region becomes. Consequently, an image that becomes more precise by amount of the decrease in the shift can be obtained, but the X-ray exposure dose is not reduced very much. Also, the photography interval can also be automatically set. In that case, a setting stored in advance in the host computer 101, for example, a setting such as "One global measurement scanning is executed every 10 slices." may be used without modification. Otherwise, instead of such automatic setting, a setting such as "One normal scanning is executed every 30 slices." is also possible with the use of a manual. A setting of "No global measurement scanning is executed in the course of the continuous scanning." can also be made. At that time, the data obtained by the reference scanning executed at the above-described step 48 are embedded toward the data outside the concerned region, thereby executing the image reconstruction processing.

Figure 16:
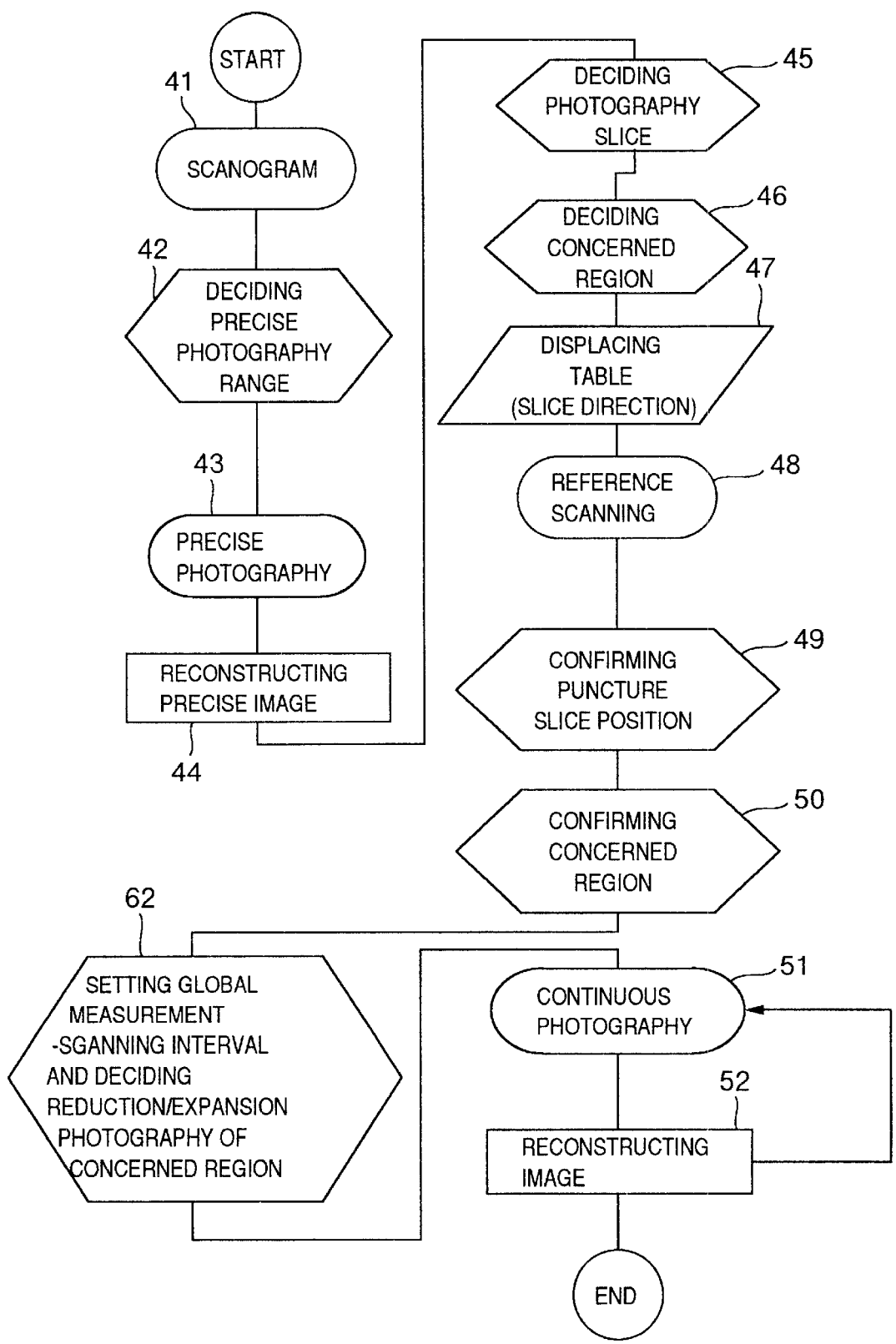
FIG. 16 is a diagram showing another embodiment of the flow of the photography in the X-ray CT in the present invention.

FIG. 16 shows an embodiment of flow of the photography in which the photography is executed while moving the channel collimator. The same number is allotted to the same step as that in FIG. 8.

Namely, after the confirming of the concerned region (step 50), at a step 62, together with the setting of the global measurement-scanning interval, it is further made possible to make a setting of expansion photography of the concerned region. Namely, if a reduction/expansion setting is selected here, between the concerned region photography and the global measurement scanning, the concerned region A and the region for the global measurement scanning gradually come close to each other. In other words, it is possible to execute a scanning the measuring range of which is gradually reduced from the global measurement scanning range or a set range to the concerned region A.

Also, in the case of the expansion, the measuring range is gradually expanded from the concerned region A to the normal scanning region or the set range.

Also, in the case of the reduction, assuming that the concerned region A is of a circular shape, a circle of the global measurement scanning range or the set range is gradually reduced and, finally, the measuring range attains to the concerned region A (In the case of the expansion, the measuring range is altered in the reverse way.). Moreover, data fetched outside the concerned region A while reducing (or expanding) are used for the correction of the image reconstruction explained above, thereby making it possible to achieve the high picture quality of the image in the region outside the concerned region A.

In the present embodiment, when selecting the reduction/expansion photography, it turns out that a radius of the above-described circle of the concerned region A or a central coordinate of the concerned region A, in some cases, is altered during the scanning. As is illustrated in FIG. 6, however, it is obvious that, under the control of the channel collimator 210 according to the above-described embodiment, it is operable when the central coordinate of the concerned region A is shifted from the center of rotation of the X-ray source.

Figure 17:
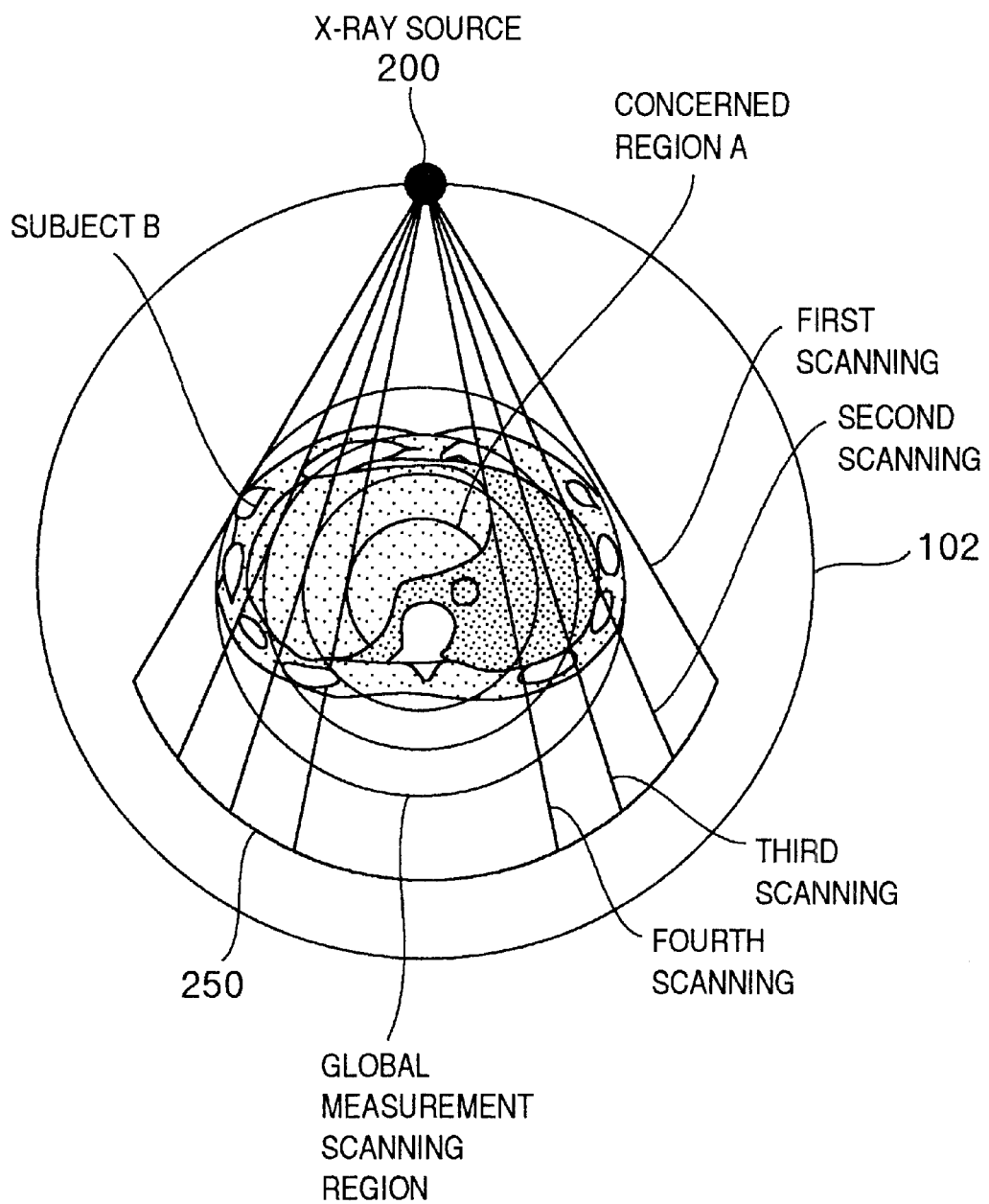
FIG. 17 is an illustrative diagram of reduction/expansion photography of the concerned region in the embodiment in FIG. 16.

However, making an assumption that, for simplicity, the central coordinate of the concerned region A coincides with the center of rotation of the X-ray source, the explanation will be given below concerning the operation in the case where the reduction/expansion photography is selected. Additionally, the assumption results in a condition that a value of the radius r of the concerned region A becomes an only parameter that is altered. FIG. 17 illustrates a photography situation where, in this way, the photography range of the concerned region A is gradually reduced (or expanded).

As illustrated in FIG. 17, in the course of a scanning such as the continues scanning or the fluoroscopy photography, a photography is executed with the channel collimator 210 gradually reduced from the global measurement scanning range to the concerned region A or gradually expanded from the concerned region A to the global measurement scanning range. By this, a high picture quality can be obtained by embedding only the data in a region unobtainable by the local measurement scanning with the projection data obtained by the global measurement scanning and a singular or a plurality of projection data obtained previously in time.

This processing will be explained below, using projection data at the time when, for simplicity, the scanner 102 has been rotated one turn and the X-ray source 200 is directly above the concerned region as is illustrated in FIG. 17. Namely, now, it is assumed that the X-ray irradiation range is gradually reduced from the normal scanning region to the concerned region A for each of the turns of the scanner. According to this assumption, projection data obtained by the respective scannings (i.e., the first scanning to the fourth scanning) are given as illustrated in FIG. 18.

Figure 18:
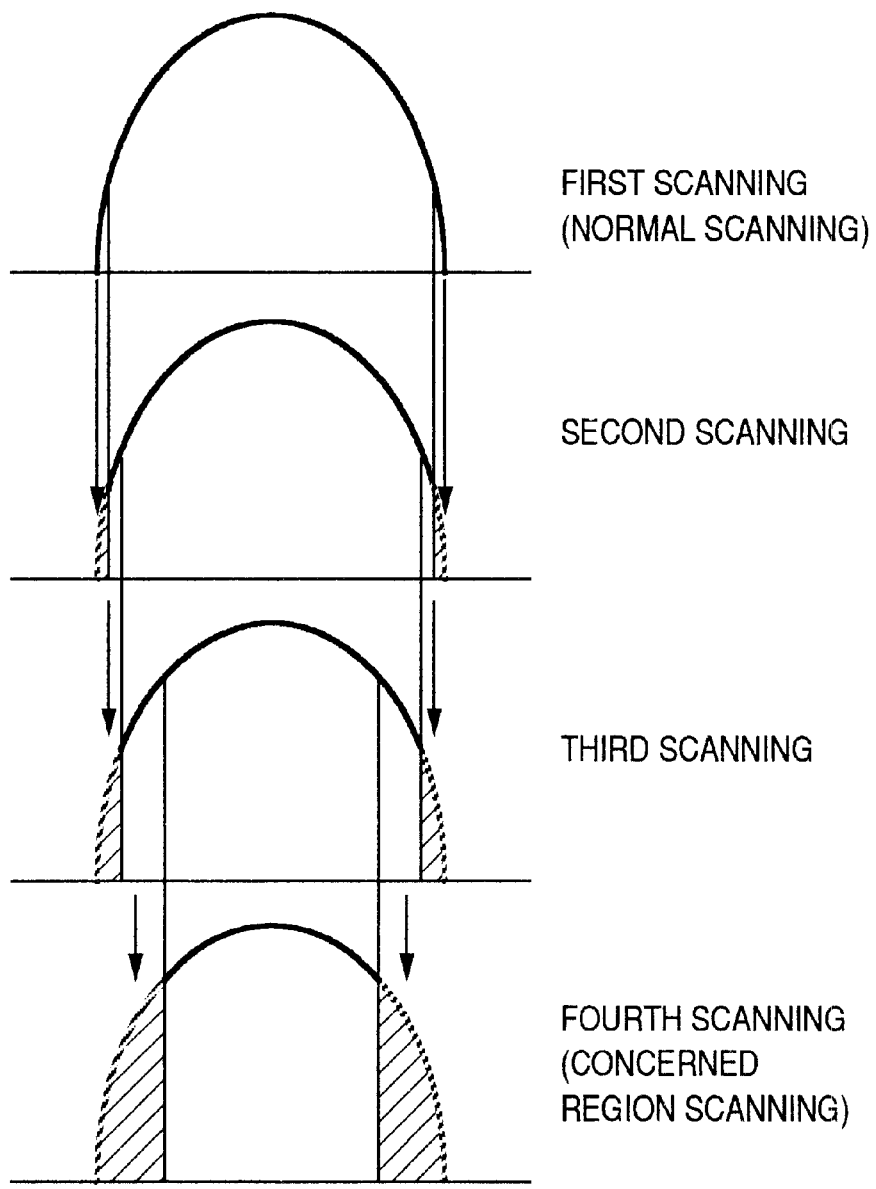
FIG. 18 is a diagram explaining the image reconstruction at the time of the reduction photography.

Namely, in FIG. 18, the bold solid lines indicate the respective effective data ranges. Concretely, first, the effective data range in the first scanning is the widest, and, conversely, the effective data range in the fourth scanning (a scanning for the concerned region A) becomes the narrowest. As to the data obtained in the second scanning, the projection data in regions shielded by the collimator are compensated with projection data in the above-mentioned first scanning. Moreover, the projection data in the second scanning, including the above-mentioned projection data embedded from the first scanning in the projection data in the second scanning, are embedded in projection data in regions shielded by the collimator in data obtained by the third scanning. Furthermore, the projection data in the third scanning are embedded in data in the fourth scanning.

In this way, according to the present embodiment, the projection data in the first and the second scannings are included in the projection data in the third scanning. Consequently, it turns out that the data in regions shielded by the collimator in the fourth scanning are constructed by being compensated with the data in the first to third scannings. Namely, the above-mentioned image reconstructing procedure means that, using the data that are nearer in time, the data are embedded one after another. This allows the image outside the concerned region A as well to be reconstructed as a high picture quality image.

Incidentally, the above-mentioned explanation in FIG. 18 has been given concerning only the case where the measuring region is reduced. The present invention, however, is not limited thereto. As will be explained below using FIG. 19, a method is also possible that executes the image reconstruction based on both the reduction photography and the expansion photography of the measuring region.

Figure 19:
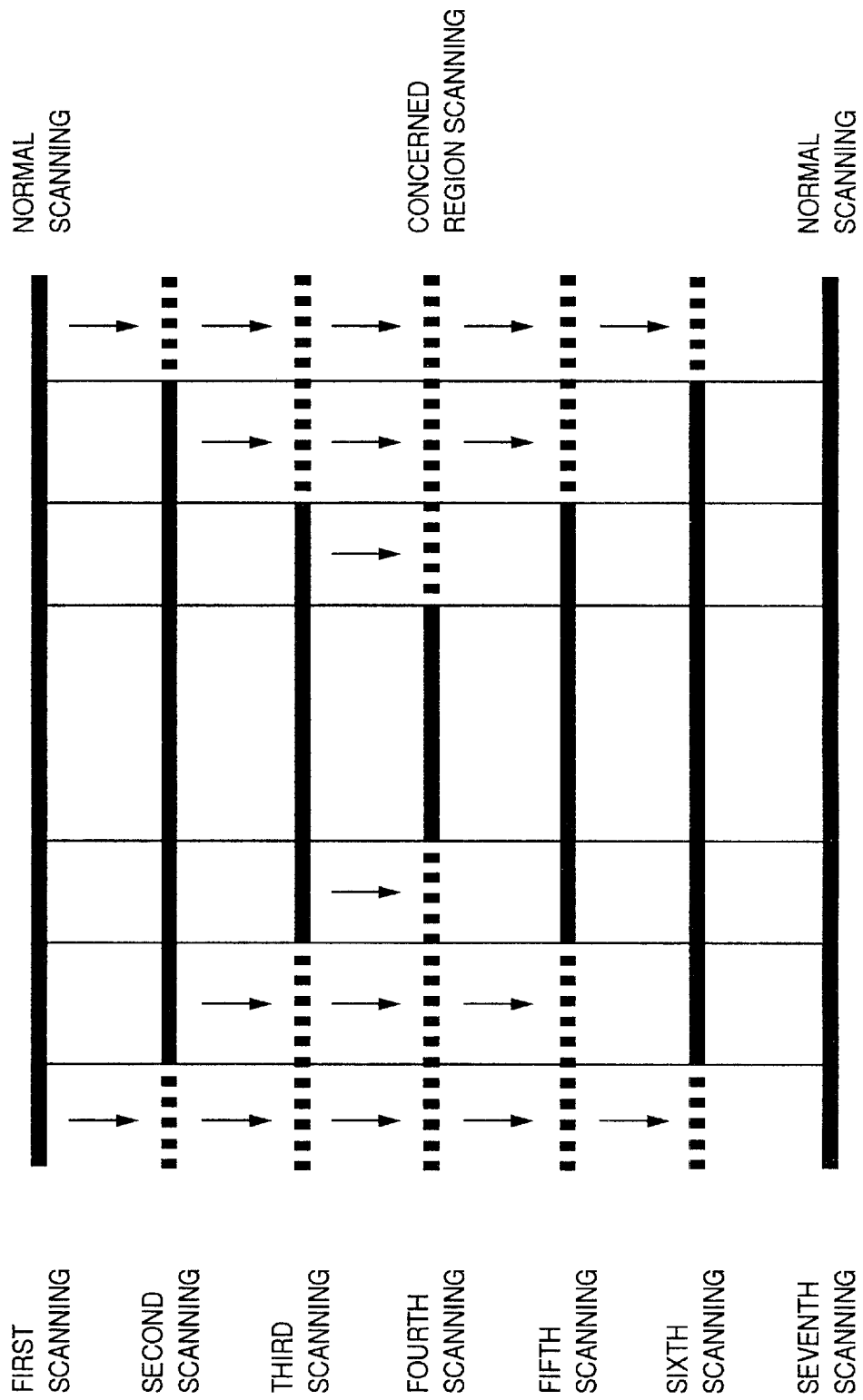
FIG. 19 is a diagram explaining the image reconstruction at the time. of the reduction/expansion photography in the embodiment in FIG. 16.

In FIG. 19, for explanation, straight lines represent projection data obtained by the measurement. Namely, the bold solid lines in the drawing indicate the effective data ranges that are actually obtained (i.e., not shielded by the channel collimator), and dashed lines indicate the data in ranges that are not measured. In the explanation in FIG. 19, the following assumption has been made: The first to the seventh scannings are executed, and each of the scannings indicates projection data obtained at the first projection angle in the first scanning, and the measuring range thereof is altered for each of the scannings. Also, as is apparent from the drawing, the first and the seventh scannings are global measurement scannings, and the fourth scanning is a scanning for only the concerned region A.

In these projection data, the procedure in image reconstructing processings based on the first to the fourth projection data is the same as the procedure already explained, and accordingly the explanation thereof is omitted here. Moreover, in an image reconstructing processing in the fifth scanning in which an expansion scanning is executed, the data in regions shielded by the collimator are compensated with the data in the second and the first scannings, and in an image reconstructing processing in the sixth scanning, it is compensated with the data in the first scanning. Also, although not illustrated, in the seventh scanning or thereafter, the image reconstructing processings are performed using units of the above-described combined data. By doing as above-mentioned, since the data that are nearer in time are employed and embedded one after another, a high picture quality image can be reconstructed for an image of regions other than the concerned region A.

Figure 20:
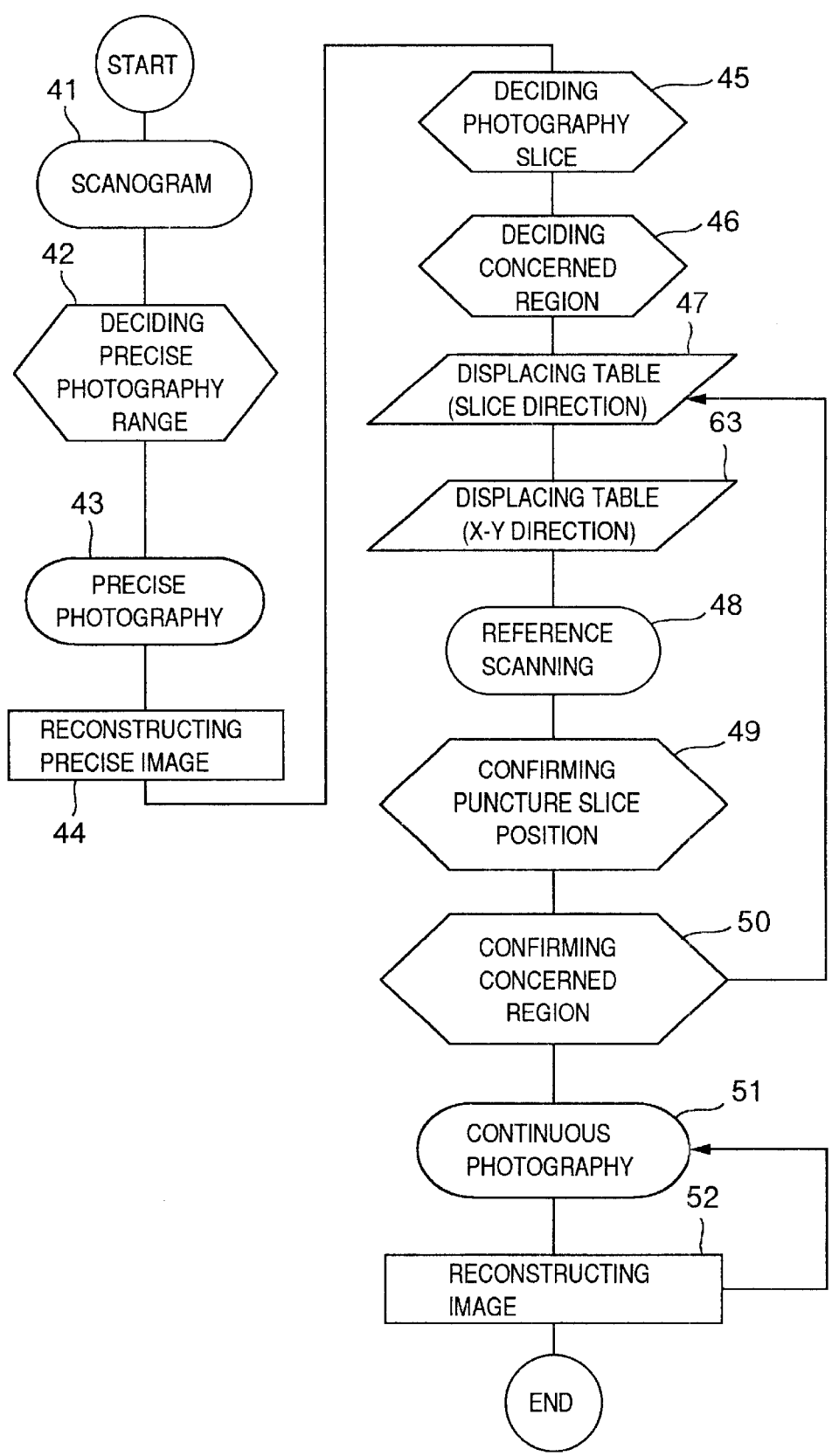
FIG. 20 is a diagram showing another embodiment of the flow of the photography in the X-ray CT in the present invention.

FIG. 20 shows another embodiment of the flow of the photography in the present invention.

In the present embodiment, a displacement amount of the patient table is determined that allows the center of a set concerned region to coincide with the center of rotation of the X-ray source, thereby making it possible to easily set the center of the concerned region to be the center of rotation of the X-ray source. As illustrated in FIG. 20, in the course of the flow of the photography in FIG. 8, there is provided a function that the host computer (101, FIG. 1) and the table controller (107, FIG. 1) automatically displace the patient table in an x-y direction (step 63). If the set field of irradiation is a circular region the center of which coincides with the center of rotation of the X-ray source, even if a measurement is made at any angle, the viewing angles become equal to each other. Thus, it is enough to set the collimator only once before the scanning. Consequently, if the irradiation range is determined, it is sufficient to execute position control of the table just one time. This makes the control easier and the reliability higher. The packing processing also becomes easier since the effective data ranges become the same at the respective view angles.

The present invention is not limited to the embodiments disclosed above but includes a variety of modifications included in the claims.

INDUSTRIAL APPLICABILITY

The present invention is applicable to fields such as an x-ray-used inspection or an x-ray photography in which it is desirable to lower the x-ray exposure dose.

What is claimed is:

1. An X-ray CT apparatus, comprising:

a display apparatus displaying a tomographic image;

means for setting a concerned region on the tomographic image displayed by said display apparatus;

X-ray shielding means for restricting an irradiation range of an X-ray fan beam in relation to said concerned region;

means for controlling said X-ray shielding means so that said irradiation range of said X-ray fan beam through said X-ray shielding means and restriction positions of said X-ray shielding means are controlled in response to a rotation angle of an X-ray irradiator;

means for, through said X-ray shielding means, irradiating with X-rays from said X-ray irradiator a range including said concerned region in a subject to be inspected and executing an X-ray CT measurement; and means for obtaining outside of concerned region data by means of calculation and reconstructing an image with the use of said outside of concerned region data and data of the irradiation range restricted by said X-ray shielding means, said outside of concerned region data being data of a range that is not restricted by said X-ray shielding means.

2. The X-ray CT apparatus as claimed in claim 1, wherein said means for controlling said X-ray shielding means controls a position of said X-ray shielding means and comprises a table that stores data on the restriction positions of said X-ray shielding means for each predetermined rotation angle of said X-ray irradiation means.

3. The X-ray CT apparatus as claimed in claim 1, further comprising means for controlling a position of a subject-mounting table so that a center of said concerned region coincides with a center of rotation of an X-ray source.

4. The X-ray CT apparatus as claimed in claim 1, wherein said means for reconstructing an image comprises means for reconstructing said image with the use of previously measured data as said outside of concerned region data.

5. The X-ray CT apparatus as claimed in claim 4, wherein said previously measured data includes data obtained by a global measurement scanning.

6. The X-ray CT apparatus as claimed in claim 1, wherein said means for reconstructing an image comprises means for reconstructing said image with the use of data obtained by calculation from data obtained by said measurement in the X-ray irradiation range in addition to said data obtained by said measurement.

7. The X-ray CT apparatus as claimed in claim 6, wherein said means for reconstructing an image comprises means for obtaining data for image reconstruction through an extrapolation of said data obtained by said measurement in the X-ray irradiation range.

8. The X-ray CT apparatus as claimed in claim 1, wherein said means for controlling a position of said X-ray shielding means comprises means for controlling the position of said X-ray shielding means so that, when a plurality of continuous measurements are executed, a region outside of said concerned region is also irradiated with X-rays at least one time.

9. An X-ray CT apparatus, comprising:
- a display apparatus displaying a tomographic image;
- means for setting a concerned region on the tomographic image displayed by said display apparatus; X-ray shielding means for restricting an irradiation range of an X-ray fan beam in relation to said concerned region;
- means for controlling said X-ray shielding means;
- means for, through said X-ray shielding means, irradiating with X-rays a range including said concerned region in a subject to be inspected and executing an X-ray CT measurement; and
- means for obtaining outside of concerned region data by means of calculation and reconstructing an image with the use of said outside of concerned region data and data of the irradiation range restricted by said X-ray shielding means, said outside of concerned region data being data of a range that is not restricted by said X-ray shielding means;
- wherein said means for controlling a position of said X-ray shielding means comprises means for controlling the position of said X-ray shielding means so that, when a plurality of continuous measurements are executed, a region outside of said concerned region is also irradiated with X-rays at least one time; and
- wherein said means for controlling a position of said X-ray shielding means comprises means for setting the position of said X-ray shielding means so that, for each scanning, the X-ray irradiation range is gradually reduced or expanded between said concerned region and a global measurement scanning range.

10. The X-ray CT apparatus as claimed in claim 1, wherein said means for setting a concerned region comprises means for displaying a boundary of the concerned region set on said display apparatus.

11. An X-ray CT apparatus, comprising:
- an X-ray tube;
- a high voltage generator for supplying a high voltage to said X-ray tube;
- an X-ray detector opposed to and at a predetermined distance from said X-ray tube;
- a scanner mechanism unit for rotating said X-ray tube and said X-ray detector around a subject to be inspected;
- an image processor for processing measurement data and reconstructing an image;
- a display apparatus for displaying an image reconstructed;
- a slice collimator provided in an X-ray irradiation portion of said X-ray tube for restricting an X-ray irradiation range to a slice width;
- X-ray shielding means provided in said X-ray irradiation portion of said X-ray tube for restricting an X-ray irradiation range in an X-ray fan beam direction;
- a computer for controlling operations of an entire apparatus, wherein said image processor obtains outside of concerned region data by means of calculation and reconstructs said image with the use of said outside of concerned region data and data of the irradiation range restricted by said X-ray shielding means, said outside of concerned region data being data of a range that is not restricted by said X-ray shielding means; and
- means for controlling said X-ray shielding means so that said irradiation range of said X-ray fan beam through said X-ray shielding means and restriction positions of said X-ray shielding means are controlled in response to a rotation angle of an X-ray irradiation means.

12. The X-ray CT apparatus as claimed in claim 11, wherein said X-ray shielding means comprises a motor, a control unit for controlling said motor, and X-ray shielding boards capable of being extended or contracted in a horizontal direction by said motor and being provided on right and left sides, respectively, with respect to an X-ray irradiation aperture.

13. A method of reconstructing an image in an X-ray CT apparatus, comprising the steps of:
- obtaining projection data by executing X-ray irradiation with an X-ray fan beam converged onto a predetermined range by moving X-ray shielding means to predetermined positions in response to a rotation angle of an X-ray irradiation means; and
- reconstructing an image by using said projection data and correction data corresponding to a region outside of said predetermined range.

14. The method of reconstructing an image as claimed in claim 13, wherein said step of obtaining projection data comprises the steps of:
- obtaining first projection data by executing X-ray irradiation with the X-ray fan beam converged onto a first range; and
- obtaining second projection data by executing X-ray irradiation with the X-ray fan beam converged onto a second range that is narrower than said first range, and said step of reconstructing an image comprises a step of, when said image is reconstructed on the basis of said second data, reconstructing an image outside of said second range by using said first data corresponding to a region outside of said second range.

15. The method of reconstructing an image as claimed in claim 13, wherein said step of reconstructing an image comprises a step of obtaining correction data corresponding to a region outside of said predetermined range through an extrapolation from said projection data.

16. The method of reconstructing an image as claimed in claim 13, wherein said step of obtaining projection data comprises a step of obtaining projection data by converging, for each scanning, said X-ray fan beam onto any. one of at least two ranges that are different in size, one of the at least two ranges being narrow and the other of the at least two ranges being wide, and
said step of reconstructing an image comprises a step of, when said image is reconstructed on the basis of projection data obtained with said X-ray fan beam converged onto the narrow range, reconstructing said image by using, as said correction data, data of a corresponding portion of projection data that is the nearest in time among projection data obtained previously with said X-ray fan beam converged onto the wide range.

17. The method of reconstructing an image as claimed in claim 13, wherein said step of obtaining projection data comprises a step of obtaining projection data by converging, for each scanning, said X-ray fan beam onto any one of at least two ranges that are different in size, at least said two ranges including an irradiation range in the case of not converging said X-ray fan beam and an irradiation range in the case of converging said X-ray fan beam up to a concerned region, and said step of reconstructing an image comprises a step of, when a measurement is executed without converging said X-ray fan beam, reconstructing said image by using projection data obtained by said measurement, and when a measurement is executed with said X-ray fan beam converged, reconstructing said image by using, as said correction data, data of a corresponding portion of projection data that is the nearest in time among projection data obtained by a previous measurement.

18. The method of reconstructing an image as claimed in claim 13, wherein said step of obtaining projection data comprises the step of obtaining said projection data by a global measurement scanning in which said X-ray fan beam is not restricted and a local measurement scanning in which said X-ray fan beam is restricted onto a range of a concerned region, and said step of reconstructing an image comprises a step of, when said image is reconstructed using said projection data obtained by said local measurement scanning, reconstructing said image by using, as said correction data, data of a corresponding portion of said projection data obtained by said global measurement scanning.

19. The method of reconstructin an image as claimed in claim 13, wherein said step of obtaining projection data comprises the steps of:

setting a concerned region on a tomographic image; and setting said concerned region as one of said predetermined range.

20. The method of reconstructing an image as claimed in claim 19, further comprising, before said step of obtaining projection data, a step of moving a position of a subject-mounting table so that a center of said concerned region coincides with a center of rotation of an X-ray source.

21. An X-ray CT apparatus, comprising:

a display apparatus for displaying a tomographic image, means for setting a concerned region on the tomographic image displayed by said display apparatus;

X-ray shielding means for restricting an irradiation range of an X-ray fan beam in relation to said concerned region;

means for controlling said X-ray shielding means so that said irradiation range of said X-ray fan beam through said X-ray shielding means is controlled in response to a rotation angle of an X-ray irradiator;

means for, through said X-ray shielding means, irradiating with X-rays from said X-ray irradiator a range including said concerned region in a subject to be inspected and executing an X-ray CT measurement; and means for reconstructing an image from data obtained by said measurement, wherein said means for reconstructing an image comprises means for reconstructing said image with the use of data obtained by calculation from data obtained by said measurement in the X-ray irradiation range in addition to said data obtained by said measurement.

22. The X-ray CT apparatus as claimed in claim 21 wherein said means for reconstructing an image comprises means for obtaining data for image reconstruction through an extrapolation from said data inside the X-ray irradiation range that is obtained by said measurement.

23. An X-ray CT apparatus, comprising:

a display apparatus for displaying a tomographic image;

means for setting a concerned region on the tomographic image displayed by said display apparatus;

X-ray shielding means for restricting an irradiation range of an X-ray fan beam in relation to said concerned region;

means for controlling a position of said X-ray shielding means;

means for, through said X-ray shielding means, irradiating with X-rays a range including said concerned region in a subject to be inspected and executing an X-ray CT measurement; and means for reconstructing an image from data obtained by said measurement, wherein said means for controlling the position of said X-ray shielding means comprises means for controlling the position of said X-ray shielding means so that, when a plurality of continuous measurements are executed, a region outside said concerned region is also irradiated with X-rays at least one time, and further means for setting the position of said X-ray shielding means so that, for each scanning, the X-ray irradiation range is gradually reduced or expanded between said concerned region and a global measurement scanning range.

24. An X-ray CT apparatus, comprising:

a display apparatus for displaying a tomographic image;

means for setting a concerned region on the tomographic image displayed by said display apparatus;

X-ray shielding means for restricting an irradiation range of an X-ray fan beam in relation to said concerned region;

means for controlling said X-ray shielding means;

means for, through said X-ray shielding means, irradiating with X-rays a range including said concerned region in a subject to be inspected and executing an X-ray CT measurement; and means for reconstructing an image from data obtained by said measurement, wherein said means for reconstructing an image comprises filtering means for executing a filtering processing to data in proximity to a boundary of said concerned region among said data obtained by said measurement.

25. An X-ray CT apparatus, comprising:

a display apparatus for displaying a tomographic image;

means for setting a concerned region on the tomographic image displayed by said display apparatus;

X-ray shielding means for restricting an irradiation range of an X-ray fan beam in relation to said concerned region;

means for controlling a position of said X-ray shielding means;

means for, through said X-ray shielding means, irradiating with X-rays a range including said concerned region in a subject to be inspected and executing an X-ray CT measurement; and means for reconstructing an image from data obtained by said measurement, wherein said means for reconstructing an image comprises threshold value processing means for obtaining, by means of a threshold value processing, a boundary of said concerned region of said data obtained by said measurement.

26. An X-ray CT apparatus, comprising:

a display apparatus displaying a tomographic image;

means for setting a concerned region on the tomographic image displayed by said display apparatus; X-ray shielding means for restricting an irradiation range of an X-ray fan beam in relation to said concerned region;

means for controlling said X-ray shielding means;

means for, through said X-ray shielding means, irradiating with X-rays a range including said concerned region in a subject to be inspected and executing an X-ray CT measurement; and means for obtaining outside of concerned region data by means of calculation and reconstructing an image with the use of said outside of concerned region data and data of the irradiation range restricted by said X-ray shielding means, said outside of concerned region data being data of a range that is not restricted by said X-ray shielding means;

wherein said means for reconstructing an image obtains said outside of concerned region data from data outside the irradiation range restricted by said X-ray shielding means and data of a region determined in view of an error of said X-ray shielding means.

27. An X-ray CT apparatus, comprising:

an X-ray tube;

a high voltage generator for supplying a high voltage to said X-ray tube;

an X-ray detector opposed to and at a predetermined distance from said X-ray tube;

a scanner mechanism unit for rotating said X-ray tube and said X-ray detector around a subject to be inspected;

an image processor for processing measurement data and reconstructing an image;

a display apparatus for displaying an image reconstructed;

a slice collimator provided in an X-ray irradiation portion of said X-ray tube for restricting an X-ray irradiation range to a slice width;

X-ray shielding means provided in said X-ray irradiation portion of said X-ray tube for restricting an X-ray irradiation range in an X-ray fan beam direction; and a computer for controlling operations of an entire apparatus, wherein said image processor obtains outside of concerned region data by means of calculation and reconstructs said image with the use of said outside of concerned region data and data of the irradiation range restricted by said X-ray shielding means, said outside of concerned region data being data of a range that is not restricted by said X-ray shielding means;

wherein said means for reconstructing an image obtains said outside of concerned region data from data outside the irradiation range restricted by said X-ray shielding means and data of a region determined in view of an error of said X-ray shielding means.

* * * * *